US006121046A

United States Patent [19]
Soreq et al.

[11] Patent Number: 6,121,046
[45] Date of Patent: *Sep. 19, 2000

[54] SYNTHETIC ANTISENSE OLIGODEOXYNUCLEOTIDES TARGETED TO HUMAN ACHE

[75] Inventors: Hermona Soreq, Jerusalem; Shlomo Seidman, Neve Daniel, both of Israel; Fritz Eckstein, Gottingen, Germany; Alon Friedman, M. Post HaNeguev; Daniela Kaufer, Mevasseret Zion, both of Israel

[73] Assignee: Yissum Research Development Company of the Hebrew Yniversity of Jerusalem, Jerusalem, Israel

[*] Notice: This patent is subject to a terminal disclaimer.

[21] Appl. No.: 08/990,065

[22] Filed: Dec. 12, 1997

Related U.S. Application Data

[62] Continuation-in-part of application No. 08/850,347, May 2, 1997, which is a continuation-in-part of application No. 08/318,826, filed as application No. PCT/EP93/00911, Apr. 15, 1993, Pat. No. 5,891,725.
[60] Provisional application No. 60/035,266, Dec. 12, 1996, provisional application No. 60/037,777, Feb. 13, 1997, and provisional application No. 60/053,334, Jul. 21, 1997.

[51] Int. Cl.[7] .............................. C07H 21/04; C12Q 1/68; C12N 15/00

[52] U.S. Cl. .............................. 435/375; 435/6; 435/91.1; 435/325; 435/354; 435/455; 536/23.1; 536/24.31; 536/24.33; 536/24.5; 514/44

[58] Field of Search .................................. 800/13, 14, 18, 800/3, 9; 435/6, 91.1, 375, 325, 366, 368, 352; 536/23.1, 24.31, 24.33, 24.5

[56] References Cited

U.S. PATENT DOCUMENTS

| | | |
|---|---|---|
| 3,687,808 | 8/1972 | Merigan et al. . |
| 4,469,863 | 9/1984 | Ts'o et al. . |
| 4,511,713 | 4/1985 | Miller et al. . |
| 4,666,828 | 5/1987 | Gusella . |
| 4,683,202 | 7/1987 | Mullis . |
| 4,801,531 | 1/1989 | Frossard . |
| 5,192,659 | 3/1993 | Simons . |
| 5,272,057 | 12/1993 | Smulson et al. . |
| 5,276,019 | 1/1994 | Cohen et al. . |
| 5,455,044 | 10/1995 | Kim et al. . |
| 5,558,852 | 9/1996 | Bigner et al. . |

OTHER PUBLICATIONS

Branch TIBS 23:45–50, Feb. 1998.
Agarwal et al., "Pharmacokinetics, biodistribution, and stability of oligodeoxynucleotide phosphorothioates in mice" *Proc. Natl. Acad. Sci. USA*, 88:7595–7599 (1991).
Akhtar et al., "Interactions of antisense DNA oligonucleotide analogs with phospholipid membranes (liposomes)" *Nucleic Acids Research*, vol. 19, No. 20 pp. 5551–5559 (1991).
Baker et al., "Effects of oligo sequence and chemistry on the efficiency of oligodeoxyribonucleotide–mediated mRNA cleavage" *Nucleic Acids Research*, vol. 18, No. 12, p. 3537 (1990).
Burstein et al., *Clin. Haematol.*, 122:3–27 (1983), [n/a—will send].
Caceres and Kosik, "Inhibition of neurite polarity . . . " *Nature*, 343:461–463 (1990).
Cohen et al., *Antisense Res. & Dev.*, 2:191 (1991), [n/a—will send].
Gnatt et al., "Expression of alternatively terminated unusual human butyrylcholinesterase messenger RNA transcripts . . . " *Cancer Research*, 50:1983–1987, (1990).
Galileo et al., *J. Cell. Biol.*, 112:1285 (1991), [n/a—will send].
Iyer et al., "The automated synthesis of sulfur–containing oligodeoxyribonucletodies . . . " *J. Org. Chem.*, 55:4693–4699 (1990).
Lapidot–Lifson et al., "Cloning and antisense oligodeoxynucleotide inhibition of a human homolog . . . " *Proc. Natl. Acad. Sci., USA*, vol. 89, pp. 579–583, (1992).
Lapidot–Lifson et al., "Coamplification of human acetylcholinesterase and butyrylcholinesterase genes in blood cells . . . " *Proc. Natl. Acad. Sci., USA*, vol. 86, pp. 4715–4719 (1989).
Layer et al., "Quantitative development and molecular forms of acetyl– and butyrylcholinesterase . . . " *Journal of Neurochemistry*, 49:175–182 (1987).
Lee and Nurse, "Complementation used to clone a human homologue of the fission yeast cell cycle control gene cdc2" *Nature*, 327:31–35 (1987).
Loke et al., "Characterization of oligonucleotide transport into living cells" *Proc. Natl. Acad. Sci., USA*, 86:3474–3478 (1989).
Malinger et al., "Cholinoceptive properties of human primordial, preantral, and antral oocytes . . . " *J. Mol. Neurosci.*, 1:77–84 (1989).

(List continued on next page.)

*Primary Examiner*—John L. LeGuyader
*Assistant Examiner*—Karen A. Lacourciere
*Attorney, Agent, or Firm*—Kohn & Associates

[57] ABSTRACT

A synthetic nuclease resistant antisense oligodeoxynucleotide (AS-ODN) capable of selectively modulating human acetylcholinesterase (AChE) production and a composition comprising at least one AS-ODN as an active ingredient. A nuclease resistant antisense targeted against the splice junction in the AChE mRNA post-splice message is disclosed. The synthetic nuclease resistant AS-ODNs are capable of selectively modulating human AChE production in the central nervous system or capable of selectively reducing human AChE deposition of the neuromuscular junction. The present invention also provides a method to restore balanced cholinergic signalling in the brain and spinal cord or reduce AChE in the neuromuscular junction in patients in need of such treatment by administering to a patient in need of such treatment a therapeutically effective amount of at least one of the synthetic nuclease resistant AS-ODN capable of selectively modulating human AChE production.

14 Claims, 12 Drawing Sheets

OTHER PUBLICATIONS

Moffat, "Making sense of antisense" *Science*, 253:510 (1991).

Morrison, *Neuroscience Facts*, 3:3 (1992), [n/a—will send].

Morrison, "Suppression of basic fibroblast growth factor expression by antisense oligodeoxynucleotides . . . " *J. Biol. Chem.*, 266:728 (1991).

Owens and Bunge, "Schwann cells infected with a recombinant retrovirus expressing myelin–associated glycoprotein . . . " *Neuron*, 7:565–575 (1991).

Patinkin et al., "Manipulations of cholinesterase gene expression modulate murine megakaryocytopoiesis in vitro" *Molecular and Cellular Biology*, 10:6046–6050 (1990).

Pieken et al., "Kinetic characterization of ribonuclease–resistant 2'–modified hammerhead ribozymes" *Science*, 253:314 (1991).

Prody et al., "Isolation and characterization of full–length cDNA clones coding for cholinesterase from fetal human tissues" *Proc. Natl. Acad. Sci. USA*, 84:3555–3559 (1987).

Rakonczay and Brimijoin, "Biochemistry and pathophysiology of the molecular forms of cholinesterases" in *Subcellular Biochemistry*, edited by J.R. Harris, Plenum Publishing, vol. 12, p. 335 (1988).

Shaw et al., "Modified deoxyoligonucleotides stable to exonuclease degradation in serum" *Nucleic Acids Research*, 19:747–750 (1991).

Soreq et al., "Molecular cloning and construction of the coding region for human acetylcholinesterase . . . " *Proc. Natl. Acad. Sci. USA*, 87:9688–9692 (1990).

Soreq et al., "Expression and tissue–specific assembly of human butyrylcholine esterase . . . " *J. Biol. Chem.*, 264:10608–10613 (1989).

Weinstein et al., "Suppression by antisense mRNA demonstrates a requirement for the glial fibrillary acidic protein" *J. Cell. Biol.*, 112:1205 (1991).

Whitesell et al., "Episome–generated n–myc antisense RNA restricts the differentiation potential . . . " *Molecular and Cellular Biology*, 11:1360–1371 (1991).

Wilson et al., in *Harrison's Principles of Internal Medicine*, 12th edition, McGraw–Hill, Inc., Chapters 268–269; 285–288 (1991), [n/a—will send].

Woolf et al., "The stability, toxicity and effectiveness of unmodified and phosphorothioate antisense oligodeoxynucleotides . . . " *Nucleic Acids Research*, 18:1763 (1990).

Yakubov et al., Mechanism of oligonucleotide uptake by cells: involvement of specific receptors? *Proc. Natl. Acad. Sci. USA*, 86:6454–6458 (1989).

Blake et al., "Hybridization arrest of globin synthesis in rabbit riticulocyte lysates and cells . . . " *Biochem.*, 24:6139–6145 (1985).

Burstein et al., "Quantitation of megakaryocytopoiesis in liquid culture by enzymatic determination of acetylcholinesterase" *J. Cell. Physiol.*, 122:159–165 (1985).

Burstein et al., "Megakaryocytopoiesis in culture: modulation by cholinergic mechanisms" *J. Cell. Physiol.*, 103:210–208 (1980).

Calabretta et al., "Normal and leukemic hematopoietic cells manifest differential sensitivity to inhibitory effects of c–myb antisenst . . . " *Proc.Natl.Acad.Sci.USA*, 88:2351–2355 (1991).

Chiang et al., "Antisense oligonucleotides inhibit intercellular adhesion molecule 1 expression . . . " *J. Biol. Chem.*, 266:18162–18171 (1991).

Cooney et al., "Site–specific oligonucleotide binding represses transcription of the human c–myc gene in vitro" *Science*, 241:456 (1988).

Eckstein, "Nucleoside phosphorothioates" *Ann.Rev.Biochem.*, 54:367–402 (1985).

Eguchi, "Antisense RNA" *Ann.Rev.Biochem.*, 66:631–52 (1991).

Galileo et al., "Retrovirally introduced antisense integrin RNA inhibits neuroblast migration in vivo" *Neuron*, 9:1117–1131 (1992).

Haselhoff and Gerlach, "Simple RNA enzymes with new and highly specific endoribonuclease activities" *Nature*, 334:585–591 (1988).

Layer and Sporns, "Spatiotemperoal relationship of embryonic cholinesterases with cell proliferation in chicken . . . " *Proc.Natl.Acad.Sci.USA*, 84:284–288 (1987).

Leonetti et al., "Intracellular distribution of microinjected antisense oligonucleotides" *Proc.Natl.Acad.Sci.USA*, 88:2702–2706 (1991).

Moffat, "Making sense of antisense" *Science*, 253:510–511 (1991).

Moffat, "Triplex DNA finally comes of age" *Science*, 252:1374–1375 (1991).

Moreno and Nurse, "Substrates for p34$^{cdc2}$: in vivo veritas?" *Cell*, 61:549–551 (1990).

Nielsen et al., "Sequence–selective recognition of DNA by strand displacement with a thymine–substituted polyamide" *Science*, 254:1497–1500 (1991).

Rangini et al., "CHox E, a chicken homeogene of the H2.0 type exhibits dorso–ventral restriction . . . " *Mechanisms of Development*, 35:13–24 (1991).

Sarver et al., "Ribozymes as potential anti–HIV–1 therapeutic agents" *Science*, 247:1222–1225 (1990).

Spitzer and Eckstein, "Inhibition of deoxyribonucleases by phosphorothioate groups in oligodeoxyribonucleotides" *Nucleic Acids Res.*, 16:11691–11704 (1988).

Szczylik et al., "Selective inhibition of leukemia cell proliferation by BCR–ABL antisense oligodeoxynucleotides" *Science*, 253:562–565 (1991).

Wilkinson et al., "Expression of the proto–oncogene int–1 is restricted to specific neural cells . . . " *Cell*, 50:79–88 (1987).

Andres et al., 1997. ACHE transgenic mice display embryonic modulations in spinal cord CHAT and neurexin gene expression followed by late–onset neuromotor deterioration. Proc. Natl. Acad. Sci. USA 94, 8173–8178.

Berri et al., (1997; Submitted for publication). Enhanced hemicholinium binding and attenuated dendrite branching in cognitively impaired ACHE transgenic mice.

Bennett et al., 1994, Inhibition of endothelial cell adhesion molecule expression with antisense oligonucleotides. *J. Immunol.* 152:3530–3540.

Boado and Pardridge, 1992. Complete protection of antisense oligonucleotides against serum nuclease degradation by an avidin–biotin system. Bioconjug. Chem. 3, 519–523. [n/a—will mail in].

Coleman and Taylor, 1996. Regulation of acetylcholinesterase expression during neuronal differentiation. *J. Biol. Chem.* 271:4410–4416.

Coyle, et al, 1983. Alzheimer's diseases: A disorder of cortical cholinergic innervation. Science 219:1184–1190.

Ellman et al., 1961. A new and rapid colorimetric determination of acetylcholinesterase activity. *Biochem. Pharmacol.* 7:88–95.

Greene and Tischler, 1976. Establishment of a noradrenergic clonal line of rat adrenal phaoechromocytoma cells which respond to nerve growth factor. *Proc. Natl. Acad. Sci. USA.* 73:2424–2428.

Jasmin et al. (1993) "Compartmentalization of acetylcholinesterase mRNA and enzyme at the vertebrate neuromuscular junction" *Neuron.* 11:467–477.

Johansson and Nordberg, 1993. Pharmacokinetic studies of cholinesterase inhibitors. Acta neurol. scad. Suppl. 149:22–25. [n/a—will mail in].

Julliano and Ahtar, 1992. Liposomes as a drug delivery system for antisense oligonucleotides. Antisense Res. Develop 2, 165–176. [n/a—will mail in].

Lee et al., 1995. Comparative expressed–sequences–tag analysis of differential gene expression profiles in PC–12 cells before and after nerve growth factor treatment. *Proc. Natl., Acad. Sci. USA* 92:8303–8307.

Loewenstein–Lichtenstein, et al, 1996. Overlapping drug interaction sites of human butyrylcholinesterase dissected by site–directed mutagenesis. Mol. Pharmacol. 50:1423–1431. [n/a—will mail in].

Loewenstein–Lichtenstein, et al, 1995. Genetic predisposition to adverse consequences of anto–cholinesterases in "atypical" BCHE carriers. Nature Medicine 1:1082–1085.

Owens and Bunge, 1991. *Neuron,* 7:565–575.

Rogers, et al, 1996. The efficacy and safety of Donepezil in patients with Alzheimers disease: results of a US multicentre, randomized, double blind, placebo controlled trial. Dementia 7:293–303. [n/a—will mail in].

Salpeter (1967) "Electron microscope radioautography as a quantitative tool in enzyme cytochemistry I: The distribution of acetylcholinesterase at motor endplates of a vertebrate twitch muscle" *J. Cell. Biol.* 32:379–389. [n/a—will mail in].

Seidman, et al., 1995. Synaptic and epidermal accumulations of human acetylcholinesterase are encoded by alternative 3'–terminal exons. *Mol. Cell. Biol.* 15:2993–3002.

Tao–Cheng et al., 1995. Characterization of synaptic vesicles and related neuronal features in nerve growth factor and ras oncogene differentiated PC12 cells. *J. Neurosci. Res.* 42:323–334.

Winker, 1994. Tacrine for Alzheimer's disease; which patient, what dose? JAMA 271: 1023–1024.

Agrawal, 1996. Antisense oligonucleotides: towards clinical trials, *TIBTECH,* 14:376.

Beeri et al., 1995. Transgenic expression of human acetylcholinesterase induces progressive cognitive deterioration in mice. *Current Biology,* 5:1063–1071.

Ben Aziz–Aloya et al., 1993. Expression of a human acetylcholinesterase promoter–reporter construct in developing neuromuscular junctions of Xenopus embryos, *Proc. Natl. Acad. Sci. USA,* 90:2471–2475.

Betz et al., 1994, Basic Neurochem. Molecular Cell, (Raven Press Ltd, NY) 5th Ed., 681–699.

Birikh et al, 1997. Probing Accessible Sites for Ribozymes on Human Acetylcholinesterase RNA, *RNA* Apr., 1997 pp. 429–437.

Brem et al., 1993. Polymers as controlled drug delivery devised for the treatment of malignant brain tumors, *Eur. J. Pharm. Biopharm* 39:2–7.

Bickel, et al., 1993. Pharmacologic effects in vivo in brain by vector–mediated peptide drug delivery, *Proc. Natl. Acad. Sci. USA* 90(7)2618–2622.

Calabretta, et al, 1996. Antisense strategies in the treatment of leukemias, *Semin. Oncol.,* 23:78.

Crooke, 1995. Progress in antisense therapeutics, *Hematol. Pathol.,* 2:59. [*n/a—will mail in].

Darboux, et al., 1996. The structure–function relationships in Drosophila neurotactin shows that cholinesterasic domains may have adhesive properties, *EMBRO J.,* 15:4835–4834.

Ehrlich et al., 1994. Use of partially phosphorothioated "Antisense" oligodeoxynucleotides for sequence–dependent modulation of hematopoiesis. *Antisense Res. Develop.,* 4:173–183.

Gewirtz, 1993. Oligodeoxynucleotide–based therapeutics for human leukemias, *Stem Cells Dayt.,* 11:96.

Grifman et al., 1995. Impairment of neurite extension and apoptosis–dependent DNA fragmentation in primary neuronal cell cultures administered with an ACHE antisense oligonucleotide (Abstract) *J. Neurochem.,* 65 (supplement) S82D.

Grifman et al., 1997. Potential antisense oligonucleotide therapies for neurodegenerative diseases. In *Concepts in Gene Therapy,* M. Strauss and J.A. Barranger, eds. (Walter de Gruyter & Co., Berlin).

Hanania, et al 1995. Recent advances in the application of gene therapy to human disease, *Am. J. Med.,* 99:537.

Jones et al., 1995. The effect of acetylcholinesterase on outgrowth of dopaminergic neurons in organotypic slice culture of rat midbrain, *Cell Tissue Res.,* 279:323–330.

Karpel et al. 1994. Expression of three alternative acetylcholinesterase messenger RNAs in human tumor cell lines of different tissue origins, *Exptl. Cell Res.,* 210:268–277.

Karpel et al, 1996. Overexpression of alternative human acetylcholinesterase forms modulates process extensions in cultured glioma cells, *J. Neurochem.* 66:114–123.

Knapp et al., 1994. A 30–week randomized controlled trial of high–dose tactine in patients with Alzheimer's disease. *JAMA,* 271:985–991.

Lapidot–Lifson, et al, 1992. Cloning and antisense oligodeoxynucleotide inhibition of a human homolog of cdc2 required in hematopoiesis, *Proc. Natl. Acad. Sci USA,* 89:579.

Layer, 1995. Non–classical roles of cholinesterases in the embryonic brain and possible links to Alzheimer disease, *Alzheimer Disease and associated disorders,* 9:29.

Lefebvre–D'Hellencourt, et al, 1995. Immunomodulation by cytokine antisense oligonucleotides, *Eur. Cytokine Netw.,* 6:7. [*n/a—will mail in].

Legay et al. 1993a. Cloning and expression of a rat acetylcholinesterase subunit: generation of multiple molecular forms, complementarity with a Torpedo collagenic subunit, *J. Neurochem.* 60:337–346.

Legay et al. 1993b. Expression of a cDNA encoding the glycolipid–anchored form of rat acetylcholinesterase, *FEBS Lett* 315:163–166.

Lev–Lehman et al., 1994. Antisense inhibition of acetylcholinesterase gene expression causes transient hematopoietic alterations in vivo. *Gene Therapy,* 1:127–135.

Lev–Lehman et al., 1997. Antisense Oligomers in vitro and in vivo. In *Antisense Therapeutics,* A. Cohen and S. Smicek, eds (Plenum Press, New York).

Li et al., 1991. Gene structure of mammalian acetylcholinesterase: Alternative exons dictate tissue specific expression, *J. Biol. Chem.* 266:23083–23090.

Li et al., 1993. Tissue–specific Expression and Alternative mRNA Processing of the Mammalian Acetylcholinesterase Gene, *J. Biol. Chem.* 268:5790–97.

Morrison, R. 1992. *Neuroscience Facts* 3:3. [*n/a—will mail in].

Pardridge, et al., 1992. Blood–brain barrier and new approaches to brain drug delivery. *West J. Med.* 156(3):281–286.

Pardridge, 1992. Recent Developments in peptide drug delivery to the brain, *Pharm. Toxicol.* 71(1):3–10.

Patinkin, et al., 1994. Antisense inhibition of butyrylcholinesterase gene expression predicts adverse hematopoietic consequences to cholinesterase inhibitors, *Cell. Mol. Neurbiol.*, 14:459.

Rosolen et al., 1990. Antisense Inhibition of Single Copy N–myc Expression Results in Decreased Cell Growth without Reduction of c–myc Protein in a Neuroepittelioma Cell Line, *Cancer Res.*, 50:6316.

Scanlon, et al., 1995. Oligonucleotides–mediated modulation of mammalian gene expression, *FASEB J.*, 9:1288.

Small, et al., 1995. Cholinergic regulation of neurite outgrowth from isolated chick sympathetic neurons in culture, *J. Neurosci.*, 15:144–151.

Soreq, et al., 1994. Antisense oligonucleotide inhibition of acetylcholinesterase gene expression induces progenitor cell expansion and suppresses hematopoietic apoptosis ex vivo, *Proc. Natl. Acad. Sci. USA*, 91:7907–7911.

Stein and Cheng, 1993. Antisense oligonucleotides as therapeutic agents—Is the bullet really magical? *Science*, 261:1004.

Sternfield, et al., 1997. Catalytic and non–catalytic acetylcholinesterase functions implied from transgenic ACHE expression in vertebrates. In *Neurotransmitter Release and Uptake*, S. Pogun ed. (Springer–Verlag, Berlin).

Wagner, 1994. Gene inhibition using antisense oligodeoxynucleotides, *Nature*, 372:333.

Winstein et al., 1991. *J. Cell Biol.*, 112:1205. [*n/a—will mail in].

Chalazonitis, A., Kessler JA, Twardzik DR, Morrison RS, 1992. *Neuroscience Facts* 3:3. (Originally cited under Morrison, J. Abstract only submitted at this time. Full article to follow).

Crooke, 1995. Progress in antisense therapeutics, *Hematol. Pathol.*, 2:59.

Galileo et al., 1992. Retrovirally Introduced Antisense Integrin RNA Inhibits Neuroblast Migration In Vivo *J. Cell. Biol.*, 112:1285. (Originally improperly cited as 1991).

Lefebvre–D'Hellencourt, et al, 1995. Immunomodulation by cytokine antisense oligonucleotides, *Eur. Cytokine Netw.*, 6:7.

Winstein et al., 1991. *J. Cell Biol.*, 112:1205. (Will submit when available).

|  | Buffer | AS1120 | AS1500 | ASmE2 |
|---|---|---|---|---|
| hAChE | | | | |
| mAChE | | | | |
| Syn | | | | |
| AChE Activity nmol/min/µg P | 18.48 28.86 | 19.26 29.99 | 3.86 16.90 | 19.52 |

Figure - 2

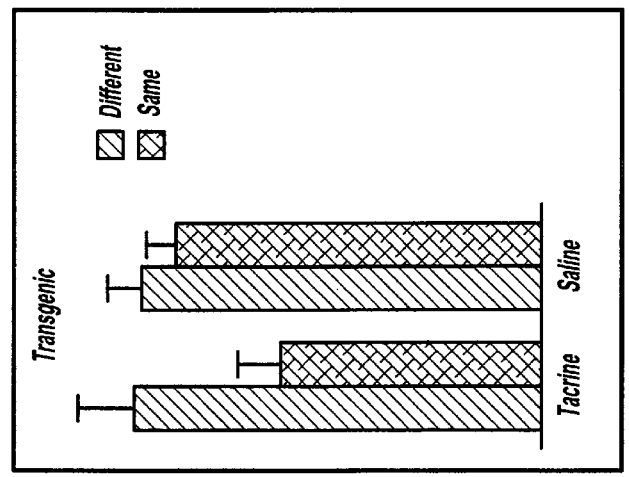
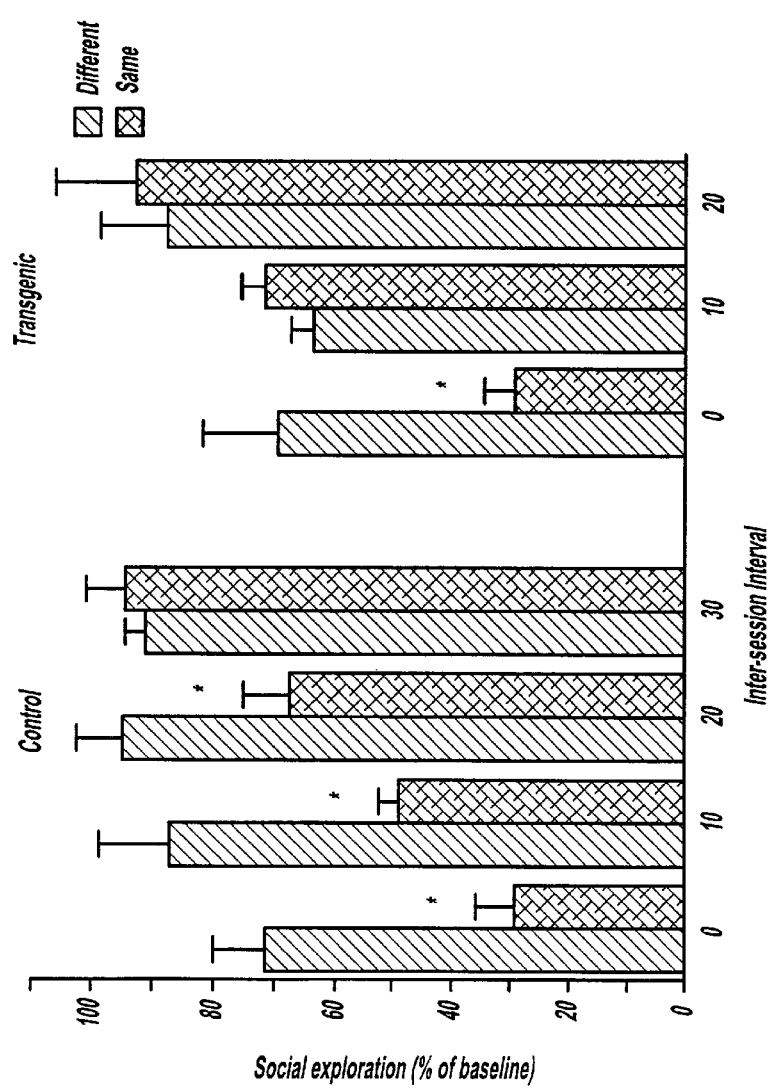
*Figure - 9B*
*Figure - 9A*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligodeoxynucleotide"

(iii) HYPOTHETICAL: NO (iv) ANTI-SENSE: YES (vi) ORIGINAL SOURCE:
            (B) STRAIN:

(xi) SEQUENCE DESCRIPTION: SEQ ID NO:1:

ACGCTTTCTT GAGGC                                                                15

(2) INFORMATION FOR SEQ ID NO:2:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:2:

GGCACCCTGG GCAGC                                                                15

(2) INFORMATION FOR SEQ ID NO:3:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

CGCGAAGCG                                                                        9

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:4:

GCCAGAGGAG GAGGAGAAGG                                                            20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear

```
        (ii) MOLECULE TYPE: other nucleic acid
             (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:5:

TAGCGTCTAC CACCCCTGAC                                                       20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:6:

CCACGTCCTC CTGCACCGTC                                                       20

(2) INFORMATION FOR SEQ ID NO:7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:7:

ATGAACTCGA TCTCGTAGCC                                                       20

(2) INFORMATION FOR SEQ ID NO:8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:8:

GGGAGAGGAG GAGGAAGAGG                                                       20

(2) INFORMATION FOR SEQ ID NO:9:

(i) SEQUENCE CHARACTERISTICS:
             (A) LENGTH: 20 base pairs
             (B) TYPE: nucleic acid
             (C) STRANDEDNESS: single
             (D) TOPOLOGY: linear
```

(ii) MOLECULE TYPE: other nucleic acid (iii) HYPOTHETICAL: NO (iv) ANTI-SENSE: YES (xi) SEQUENCE DESCRIPTION: SEQ ID NO:9:

AGAGGAGGGA CAGGGCTAAG                                                    20

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:10:

TAGCATCCAA CACTCCTGAC                                                    20

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:11:

CTGCAATATT TTCTTGCACC                                                    20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:12:

ATGAACTCGA TTTCATAGCC                                                    20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:13:

GTCGTATTAT ATCCCAGCCC                                                       20

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:14:

GTGGCTGTAA CAGTTTATTG                                                       20

(2) INFORMATION FOR SEQ ID NO:15:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:15:

GACTTTGCTA TGCAT                                                            15

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:16:

GAATCGGGAC AGGGAGGAGA                                                       20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligodeoxynucleotide"

(iii) HYPOTHETICAL: NO (iv) ANTI-SENSE: YES (xi) SEQUENCE DESCRIPTION: SEQ ID NO:17:

TCTGTGTTAT AGCCCAGCCC                                                    20

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:18:

GGCCTGTAAC AGTTTATTT                                                     19

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

GGAAGAGGAG GAGGAGACCG                                                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CCCGACCCGA TATTGTGTCT                                                    20

(2) INFORMATION FOR SEQ ID NO:21:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Leu Leu Ser Ala Thr Asp Thr Leu Asp Glu Ala Glu Arg Gln Trp Lys
1               5                   10                  15

Ala Glu Phe His Arg Trp Ser Ser Tyr Met Val His Trp Lys Asn Gln
            20                  25                  30

Phe Asp His Tyr Ser Lys Gln Asp Arg Cys Ser Asp Leu
        35                  40                  45

(2) INFORMATION FOR SEQ ID NO:22:

```
        (i) SEQUENCE CHARACTERISTICS:
            (A) LENGTH: 48 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Leu Leu Ser Ala Thr Ala Ser Glu Ala Pro Ser Thr Cys Pro Gly Phe
1               5                   10                  15

Thr His Gly Glu Ala Ala Pro Arg Pro Gly Leu Pro Leu Pro Leu Leu
                20                  25                  30

Leu Leu His Cys Leu Leu Leu Leu Phe Leu Ser His Leu Arg Arg Leu
            35                  40                  45

(2) INFORMATION FOR SEQ ID NO:23:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Leu Leu Ser Ala Thr Gly Met Gln Gly Pro Ala Gly Ser Gly Trp Glu
1               5                   10                  15

Glu Gly Ser Gly Ser Pro Pro Gly Val Thr Pro Leu Phe Ser Pro
                20                  25                  30
```

SYNTHETIC ANTISENSE OLIGODEOXYNUCLEOTIDES TARGETED TO HUMAN ACHE

CROSSREFERENCE TO RELATED APPLICATIONS

This application is a Continuation-In-Part of U.S. Ser. No. 08/850,347 filed May 2, 1997 which is a Continuation-In-Part of U.S. Ser. No. 08/318,826, filed Dec. 1, 1994, now U.S. Pat. No. 5,891,725, which is the National Phase of PCT/EP93/00911 international filing date of Apr. 15, 1993, priority Apr. 15, 1992 and U.S. Provisional Application No. 60/035,266 filed Dec. 12, 1996; Provisional Application No. 60/037,777 filed Feb. 13, 1997; Provisional Application No. 60/053,334 filed Jul. 21, 1997.

GOVERNMENT SUPPORT

Research in this application was supported in part by U.S. Department of the Army Contract DAMD17-86-C-6010. The U.S. Government has a nonexclusive, nontransferable, irrevocable paid-up license to practice or have practiced this invention for or on its behalf as provided by the terms of Contract DAMD17-86-C-6010 awarded by the U.S. Department of the Army.

BACKGROUND OF THE INVENTION

1. Field of the Invention

The field of this invention is antisense oligodeoxynucleotides and pharmaceuticals based on them.

2. Description of Related Art

The ACHE gene encoding the acetylcholine hydrolyzing enzyme acetylcholinesterase (AChE, EC 3.1.1.7) is expressed in muscle, nerve, hematopoietic cells, embryonic tissue and germ cells. ACHE maps to chromosome 7q22 and encodes the primary enzyme, acetylcholinesterase (AChE, E.C. 3.1.1.7), which terminates neurotransmission at synapses and neuromuscular junctions.

The text *Human Cholinesterases and Anticholinesterases* by Soreq and Zakut (Academic Press, Inc., 1993) provides a summation of the biochemical and biological background as well as the molecular biology of human cholinesterase genes. The text in its entirety is incorporated herein by reference. Further, the text *Transgenic Xenopus* by Seidman and Soreq (Humana Press, 1996) provides a summation of the development of the Xenopus transgenic animal model. The text in its entirety is incorporated herein by reference. Articles by Beeri et al, 1995; Karpel et al, 1996; and the review articles by Lev-Lehman et al, 1997 and Grifman et al, 1995, 1997 provide further information on the development of antisense ACHE oligomers, the parameters for choosing sequences and testing for efficacy and are incorporated herein by reference.

Briefly, AChE includes the peptide motif S/T-P-X-Z, which makes it a potential substrate for phosphorylation by cdc2 kinases, the general controllers of the cell cycle. Most other substrates of cdc2 kinases perform biological functions necessary for cell cycle-related processes. Thus, interference with either CHE or cdc2 transcription processes may be expected to divert and/or arrest cell division, and controlling these processes can be useful for several, medically important procedures.

Biochemical and histochemical analyses indicate that AChE is expressed, in high levels, in various fetal tissues of multiple eukaryotic species where cholinesterases (ChEs) are coordinately regulated with respect to cell proliferation and differentiation. The specific role to be attributed to ChEs in embryonic development may hence be related with cell division, so that their biological function(s) in these tissues are tentatively implicated in the control of organogenesis.

In addition to its presence in the membranes of mature erythrocytes, AChE is also intensively produced in developing blood cells in vivo and in vitro and its activity serves as an acceptable marker for developing mouse megakaryocytes. Furthermore, administration of acetylcholine analogues as well as cholinesterase inhibitors has been shown to induce megakaryocytopoiesis and increased platelet counts in the mouse, implicating this enzyme in the commitment and development of these hematopoietic cells.

A major hydrophilic form of AChE with the potential to be "tailed" by non-catalytic subunits is expressed in central nervous system and muscle whereas a hydrophobic, phosphoinositide (PI)-linked form of the enzyme is found in erythrocytes. Alternative exons encoding the C-terminal peptide in AChE were shown to provide the molecular origins for the amphiphilic (PI)-linked and the hydrophilic "tailed" form of AChE in Torpedo electric organ. The existence of corresponding alternative exons and homologous enzyme forms in mammals suggested that a similar mechanism may provide for the molecular polymorphism of human AChE. cDNAs reported to date from mammalian brain and muscle encode the hydrophilic AChE form.

More specifically, three alternative AChE-encoding mRNAs have been described in mammals (FIG. 11). The dominant central nervous system and muscle AChE (AChE-T) found in the neuromuscular junction (NMJ) is encoded by a mRNA carrying exon E1 and the invariant coding exons E2, E3, and E4 spliced to alternative exon E6 [Li et al., 1991; Ben Aziz-Aloya et al., 1993]. AChEmRNA bearing exons E1–4 and alternative exon E5 encodes the glycolipid phosphatidylinositol (GPT)-linked form of AChE characteristic of vertebrate erythrocytes (AChE-H;) [Li et al., 1993; Legay et al., 1993a]. An additional readthrough mRNA species retaining the intronic sequence I4 located immediately 3' to exon E4 was reported in rodent bone marrow and erythroleukemic cells [Li et al., 1993; Legay et al., 1993a] and in various tumor cells lines of human origin [Karpel et al., 1994].

AChE is the major cholinesterase (ChE) in nervous system cells. Since acetylcholine is produced mostly in the CNS, changes in AChE should be coupled to mental state.

The cholinergic theory of Alzheimer's disease [Coyle, et al, 1983; Slotkin et al., 1994] suggests that the selective loss of cholinergic neurons in Alzheimer's disease results in a relative deficit of acetylcholine in specific regions of the brain that mediate learning and memory functions and require acetylcholine to do so. The primary approach to treating Alzheimer's disease has therefore aimed to augment the cholinergic system. Reduced levels of acetylcholine in the brains of Alzheimer's patients leaves a relative excess of acetylcholinesterase, the enzyme responsible for terminating nerve impulses during normal brain activity by disposing of used acetylcholine (Soreq and Zakut, 1993). A relative excess of acetylcholinesterase accentuates the growing cholinergic deficit by further reducing the availability of acetylcholine. The most successful strategy to date for reinforcing cholinergic neurotransmission in Alzheimer's patients is pharmacological inhibition of acetylcholinesterase. Indeed, the only currently approved drugs for Alzheimer's disease are potent acetylcholinesterase inhibitors (Winker, 1994), i.e. drugs that suppress the catalytic activity of the acetylcholine hydrolyzing enzyme acetylcholinesterase (acetylcholine acetyl hydrolase, EC 3.1.1.7, AChE) [Knapp et al., 1994]. This provides augmentation of cholinergic neurotransmission, which is impaired in such patients due to the selective loss of cholinergic neurons. However, such inhibitors do not reduce the amount of AChE protein, and there are recent reports of actions of AChE, unrelated to its catalytic activity, in process extension [Small et al., 1995, Layer et al.; 1995, Jones et al., 1995; Darboux et al., 1996; Sternfeld et al., 1997] and amyloid fibril formation [Inestrosa et al., 1996].

Tacrine, the first and most well-characterized acetylcholinesterase inhibitor used for treating Alzheimer's disease offers limited palliative relief to 30–50% of mild-moderately affected Alzheimer's patients for up to 6 months [Winker, 1994; Krapp et al., 1994]. The positive, albeit partial, success of Tacrine attests to the utility of the cholinergic theory and the potential value of improved anticholinesterase treatment for Alzheimer's disease. Another approved drug, E-2020 (Aricept) has been reported to follow the same mode of action as Tacrine but at lower doses [Rogers et al., 1996]. A number of other compounds are under development for inhibition of acetylcholinesterase [Johansson and Nordberg, 1993]. All of these are aimed at blocking the fully folded protein from degrading acetylcholine.

The positive, albeit partial, success of Tacrine attests to the potential value of improved anticholinesterase treatment of Alzheimer's Disease. However, anti-acetylcholinesterase therapies for Alzheimer's Disease require high doses of drug and produce side-effects associated with systemic cholinergic toxicity. Tacrine, for example, has been associated with liver damage and blood disorders in some patients [Johansson and Nordberg, 1993]. Further, current ACHE inhibitors interact non-specifically with the AChE-homologous serum protein butyrylcholinesterase and stimulate regulatory feedback pathways leading to enhanced expression of AchE.

Although newer inhibitors such as E-2020 having greater specificity for acetylcholinesterase provide for lower doses [Rogers et al., 1996], they are not likely to completely overcome the problem of cross-reactivity with butyrylcholinesterase, given the high degree of similarity between the two proteins [Loewenstein-Lichtenstein et al., 1996]. Moreover, liver function, red blood cell counts, and natural variations in the genes encoding both acetylcholinesterase and butyrylcholinesterase will determine both the quantity and quality of the drug scavenging potential among individual patients. Several mutations in the butyrylcholinesterase gene already have been suggested to create a genetic predisposition for adverse responses to anti-cholinesterases [Loewenstein-Lichtenstein et al., 1995]. This implies that even in the best case scenario for acetylcholinesterase inhibitor-based therapies, various elements must be considered in designing individualized dosage regimens on a patient-by-patient basis.

Myasthenia gravis (MG) is an autoimmune disease in which antibodies directed against the nicotinic acetylcholine receptor (AChR) at the motor end plate of the neuromuscular junction (NMJ) by binding to the ACHR impair neuromuscular communication either directly or through NMR degradation. Therapeutic strategies for treating MG now include anticholinesterase drugs, immunosuppressive drugs, thymectomy and plasmapheresis [see Myasthenia Gravis And Related Disorders, Annals of the New York Academy of Sciences, volumes 681 (1993), 505 (1987), 377 (1981), 274 (1976) and 135 (1966) for an overview of the progress and development of the understanding of MG disease etiology and therapeutic strategies as well as the 1998 volume (in press)].

AChE is accumulated at neuromuscular junctions (Salpeter 1967) where it serves a vital function in modulating cholinergic neurotransmission (reviewed by Soreq and Zakut, 1993). The molecular mechanisms by which AChE and other synaptic proteins are targeted to the NMJ are poorly understood. Compartmentalized transcription and translation in and around the junctional nuclei probably contribute to the NMJ localization of AChE (Jasmin et al., 1993). Therefore, anticholinesterase therapy is utilized with almost all patients in order to reduce AChE and thereby increase the halflife of acetylcholine thereby potentiating neuromuscular transmission. This therapy is often used in concert with immunosuppressive therapy (generally steroids). It is the general goal to remove the patient from immunosuppressive therapy due to its side effects.

Pyridostigmine (Mestinon®) remains the drug of choice in treating myasthenics due to its effectiveness and tolerance by patients. Ambenonium (Mytelase®) is used for those MG patients who cannot tolerate pyridostigmine. However, patients must be involved in the determination of dosage of the drug since dosage will often need to be adjusted over any twenty-four hour period. Variables such as menstrual cycle, infections and emotional stress affect dosage and patients must be trained to modify their dosage to take these and other factors into consideration. Overdosage of pyridostigmine can lead to cholinergic crisis and even with good patient education such overdoses occur. Additionally, as discussed herein above genetic predispositions to predisposition for adverse responses to anti-cholinesterases [Loewenstein-Lichtenstein et al., 1995] must be considered.

Cholinergic crisis due to anticholinesterase drug overdose is characterized by increasing muscle weakness which if involving the respiratory muscles can lead to a myasthenic crisis and death. Myasthenic crisis due to increase in severity of disease can also present with the same symptoms. Distinguishing between the two is extremely important since treatment for a cholinergic crisis is termination of anticholinesterase drugs while the non-drug associated myasthenic crisis would indicate an increase in anti-cholinergic drug dosage. Therefore finding alternatives to anticholinesterase drug therapy in MG would be useful.

These considerations indicate the need to develop a new generation of anti-acetylcholinesterase drugs displaying increased target specificity, improved efficacy and reduced side effects.

Breakthroughs in molecular biology and the human genome project have opened previously unforeseen possibilities for targeted intervention with mammalian gene expression. These include permanent approaches such as transgenic overexpression or recombinant disruption of specific genes as well as novel approaches for transient suppression of gene function. Short synthetic antisense (AS) oligodeoxynucleotides (AS-ODN) designed to hybridize with specific sequences within a targeted mRNA belong to the latter class.

Many excellent reviews have covered the main aspects of antisense technology and its enormous therapeutic potential. The literature naturally progressed from chemical [Crooke, 1995] into cellular [Wagner, 1994] and therapeutic [Hanania, et al, 1995; Scanlon, et al, 1995] aspects of this rapidly developing technology. Within a relatively short time, ample information has accumulated about the in vitro use of AS-ODN in cultured primary cells and cell lines as well as for in vivo administration of such ODNs for suppressing specific processes and changing body functions in a transient manner. This wealth of accumulated experience now offers a novel way to analyze the antisense approach, namely, to compare its in vitro uses with its in vivo ones [Lev-Lehman et al, 1997]. Further, enough experience is now available in vitro and in vivo in animal models as shown in the Examples of the present application to predict human efficacy.

AS intervention in the expression of specific genes can be achieved by the use of synthetic AS-ODNs [for recent reports see Lefebvre-d'Hellencourt et al, 1995; Agrawal, 1996; Lev-Lehman et al, 1997]. AS-ODNs are short sequences of DNA (averaging 15–25 mer) designed to complement a target mRNA of interest and form an RNA:ODN duplex. This duplex formation can prevent processing, splicing, transport or translation of the relevant mRNA. Moreover, certain AS-ODNs can elicit cellular RNase H activity when hybridized with their target mRNA, resulting in mRNA degradation [Calabretta et al, 1996]. In that case, RNase H will cleave the RNA component of the duplex and can potentially release the AS-ODN to further hybridize with additional molecules of the target RNA. An additional mode of action results from the interaction of AS-ODNs with genomic DNA to form a triple helix which may be transcriptionally inactive. See FIG. 1 for a schematic representation of the modes of action of AS-ODN.

Phosphorothioate antisense oligonucleotides do not show significant toxicity and exhibit sufficient pharmacodynamic half-lives in animals [Agarwal et al., 1991, 1996]. Antisense induced loss-of-function phenotypes related with cellular development were shown for the glial fibrillary acidic protein (GFAP), implicated in astrocyte growth within astrocyte-neuron cocultures [Winstein et al., 1991], for the myelin-associated glycoprotein in Schwann cells, responsible for formation of the compact myelin sheath formation surrounding these cell [Owens and Bunge, 1991], for the microtubule-associated tau proteins implicated with the polarity of hippocampal neurons and their axon formation [Caceres and Kosik, 1990], for the $\beta_1$-integrin, important for neuronal migration along radial glial cells, and for the establishment of tectal plate formation in chick [Galileo et al., 1991] and for the N-myc protein, responsible for the maintenance of cellular heterogeneity in neuroectodermal cultures (ephithelial vs. neuroblastic cells, which differ in their colony forming abilities, tumorigenicity and adherence) [Rosolen et al., 1990; Whitesell et al, 1991]. Antisense oligonucleotide inhibition of basic fibroblast growth factor (bFgF), having mitogenic and angiogenic properties, suppressed 80% of growth in glioma cells [Morrison, 1991] in a saturable and specific manner. The antisense oligonucleotides were targeted against the initiation and splice sites in bFgFmRNA, they reduced activity of the resulting protein and sense oligomers remained inactive. In soft-agar cultures, antisense oligonucleotides reduced the size of glial colonies and induced appearance of larger cells within them [Morrison, 1992]. Being hydrophobic, antisense oligonucleotides interact well with phospholipid membranes [Akhter et al., 1991]. Following their interaction with the cellular plasma membrane, they are actively transported into living cells [Loke et al., 1989], in a saturable mechanism predicted to involve specific receptors [Yakubov et al., 1989].

SUMMARY OF THE INVENTION

According to the present invention, synthetic nuclease resistant antisense oligodeoxynucleotides capable of selectively modulating human acetylcholinesterase (AChE) production having the following sequences are disclosed:

5'ACGCTTTCTTGAGGC 3' SEQ ID No:1,
5'GGCACCCTGGGCAGC 3' SEQ ID No:2,
5'CCACGTCCTCCTGCACCGTC 3' SEQ ID No:6, and
5'ATGAACTCGATCTCGTAGCC 3' SEQ ID No:7.

Further, additional synthetic nuclease resistant antisense oligodeoxynucleotide are disclosed including 5'GCCAGAGGAGGAGGAGAAGG 3' SEQ ID No:4,
5'TAGCGTCTACCACCCCTGAC 3' SEQ ID No:5,
5'TCTGTGTTATAGCCCAGCCC 3' SEQ ID No:17, and
5'GGCCTGTAACAGTTTATTT 3' SEQ ID No:18.

A nuclease resistant antisense targeted against the splice junction in the AChEmRNA post splice message is disclosed. In an embodiment the E4–E6 junction in the E2–E3–E4–E6 splice variant AChEmRNA is disclosed as being highly specific for the muscle and central nervous system splice variant of AChE.

Synthetic nuclease resistant artisense oligodeoxynucleotides capable of selectively modulating human acetylcholinesterase production in the central nervous system or capable of selectively reducing human acetylcholinesterase deposition in the neuromuscular junction having the following sequences are also disclosed:

5'ACGCTTTCTTGAGGC 3' SEQ ID No:1,
5'GGCACCCTGGGCAGC 3' SEQ ID No:2
5'CCACGTCCTCCTGCACCGTC 3' SEQ ID No:6,
5'ATGAACTCGATCTCGTAGCC 3' SEQ ID No:7,
5'GCCAGAGGAGGAGGAGAAGG 3' SEQ ID No:4,
5'TAGCGTCTACCACCCCTGAC 3' SEQ ID No:5,
5'TCTGTGTTATAGCCCAGCCC 3' SEQ ID No:17, and
5'GGCCTGTAACAGTTTATTT 3' SEQ ID No:18.

The present invention also discloses pharmaceutical or medical composition comprising as active ingredient at least one of these synthetic nuclease resistant antisense oligodeoxynucleotides in a physiologically acceptable carrier or diluent.

The present invention further discloses a method to restore balanced cholinergic signaling in the brain in patients in need of such treatment, particularly relating to learning and memory as well as stress disorders and Parkinson's. The method includes the steps of administering to a patient in need of such treatment a therapeutically effective amount of at least one of the synthetic nuclease resistant AS-ODN of the present invention.

The present invention further discloses a method to reduce production and therefore deposition of acetylcholinesterase in the neuromuscular junction in patients in need of such treatment, particularly patients with myasthenia gravis. The method includes the steps of administering to a patient in need of such treatment a therapeutically effective amount of at least one of the synthetic nuclease resistant antisense oligodeoxynucleotides of the present invention.

This technology specifically arrests the production, as opposed to biochemical activity, of acetylcholinesterase in brain cells and prevents and/or reduces deposition at the neuromuscular junction. This technology is based on disruption of the pathway leading to acetylcholinesterase biosynthesis by administration of very low doses of antisense oligonucleotides. Antisense oligonucleotides are uniquely targeted against the gene encoding acetylcholinesterase rather than the ultimate gene product (i.e. the protein). Therefore, the molecular target of these antisense oligonucleotides against acetylcholinesterase neither interact with the related enzyme butyrylcholinesterase nor suppress butyrylcholinesterase gene expression. Hence, this potential drug works effectively at low doses while avoiding many of the side effects associated with Tacrine and related cholinergic drugs for Alzheimer's disease and pyridostigmine and related drugs for Myasthenia gravis.

DESCRIPTION OF THE DRAWINGS

Other advantages of the present invention will be readily appreciated as the same becomes better understood by reference to the following detailed description when considered in connection with the accompanying drawings wherein:

FIG. 2 is a chart with photographs of gels inserted showing reduction in AChE mRNA levels in the cortex of mice treated with antisense oligodeoxynucleotides. Specific primers were employed to detect hACHE, mACHE or synaptophysin (Syn) mRNAs; cDNA product was collected every third cycle between cycles 21–36, subjected to gel electrophoresis and stained with ethidium bromide. The products from cycles 21–36 are presented in the figure from left to right. Levels of AChE activity in cortex of mice injected with buffer or with AS oligodeoxynucleotides are presented in nmol substrate hydrolyzed/min/ug protein

FIG. 4B is a photograph of the gel electrophoresis of PCR products at various cycles and demonstrates the effect on total ACHEmRNA of antisense (AS) oligonucleotides targeted against the common exon E2 (mE2) or the alternative exon E5 (mE5) compared with those of sense (S) oligos based on the homologous human ACHE gene sequence or sham injections with PBS. β-actin mRNA served as a control for non-specific effects on transcription. Note that both AS-mE2 and AS-mE5 exert specific reduction of E6-containing ACHEmRNA in bone marrow but not muscle at the administered doses while actin mRNA was unaffected by any treatment. Gels present data from a single representative animal among three treated individuals.

FIGS. 5A–B shows anti-ACHE ODNs and their targeted ACHEmRNA sequences wherein FIG. 5A is a photograph of a gel of RT-PCR amplification products derived from total RNA preparations of adult (2 months) mouse brains, cerebral primary neurons from mouse embryos (embryonic day 13) grown in culture for 3 days with or without 0.5 μg/ml actinomycin D (Act. D) or non-differentiated PC12 cells. Shown are 10% of the products, resolved by electrophoresis on agarose slab gels and stained with ethidium bromide, of RT-PCR amplification of 200 ng RNA incubated with selective primers for the ACHEmRNA transcripts 3'-terminated with E5, E6 or I4/E5 sequences [for details, see Karpel et al., 1996]. Note that the E6-ACHEmRNA transcript is the most pronounced of all in each of these sources, and that it remains largely intact following 3 days in the presence of actinomycin D in the absence of novel transcripts. PC12 cells, like murine brain neurons, express 3 alternative ACHEmRNAs. FIG. 5B is a schematic diagram of the location and various parameters of the AS-ODNs. Location of each of the AS-ODNs ODNs (1–7) (bold underlines) is marked along the ACHE gene, which is represented schematically. Empty boxes depict introns (I) and filled boxes, exons (E) with the exception of pseudointron 4 (I4) which is also shaded. The broken lines underneath denote alternative splicing options. Open reading frame (ORF) regions are marked by a solid line above, initiated by the first AUG codon at the 5'-end of the gene. ODN structures are classified into those with no predicted secondary structure (N) and those predicted to form loops (drawn). G, C contents are also noted. Predicted melting temperatures and free energies of the ODNs are shown below each of their positions (PRIMER program, University of Wisconsin GCG software package.)

FIGS. 6A–B shows the neurotoxicity of the AS-ODNs wherein FIG. 6A is a bar graph of the survival rate of undifferentiated PC12 cells after 24 hours in the presence of either 1 μM (filled bars) or 10 μM (open bars) of each of the ODNs. Standard error of the mean for 3 cultures is shown by the error bars. Note the relatively higher toxicity of AS2, even at 1 μM, and the increased neurotoxicity at 10 μM of most other ODNs. FIG. 6B is a graph showing the linear relationship between cell number and free thiol croups. The number of non-differentiated PC12 cells deposited in microtiter wells was measured by phase microscopy and manual counting in a haemocytometer. Shown is the average absorption at 405 nm per 1,000 cells for six cultures that were exposed to buffered Triton X-100 and DTNB.

FIGS. 9A–B are bar graphs of deficient performance of AChE transgenic mice in social exploration test (A) corrected by Tacrine (B). FIG. 9A shows adult transgenic or control mice exposed to an unknown juvenile and the time invested in olfactory recognition recorded (t1). Following the indicated intervals (in minutes) each mouse was presented with the same, or a different, juvenile, and the recognition time noted (t2). Presented are the average±SD for t2/t1 for groups of 5–8 mice. Asterisk indicates statistically significant differences in t2 vs. t1. Note that transgenic mice lost the ability to recognize the "same" mouse within 10 minutes compared with 30 minutes for controls. FIG. B represents the improved memory performance observed among transgenic mice following a single administration of tacrine (1 mg/g wt) and a 20 minute interval between exposures.

DETAILED DESCRIPTION OF THE INVENTION

Figure 1:
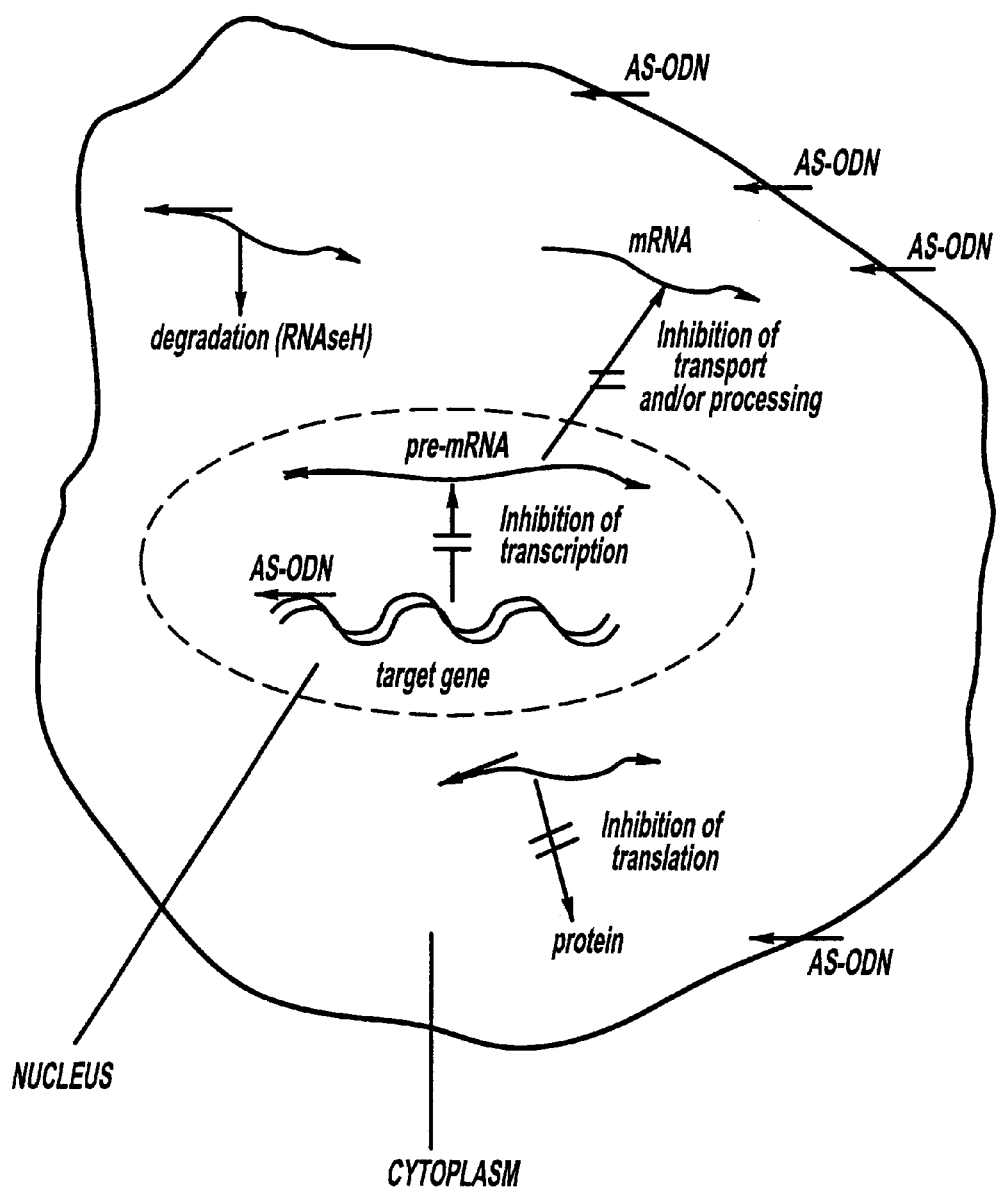
FIG. 1 is a schematic diagram of the modes of action of antisense (AS) oligodeoxynucleotides (ODN) showing a gene being transcribed into MRNA and following uptake of AS-ODN both inhibition of transcription through triple helix formation, interference with RNA splicing or translation may occur or the RNA:ODN duplex can elicit RNase H activity resulting in RNA degradation and preventing protein production.

The present invention provides a synthetic nuclease resistant antisense oligodeoxynucleotide (AS-ODN) capable of selectively modulating human acetylcholinesterase (AChE) production in the central nervous system (CNS) and neuromuscular junction (NMJ). The term modulating as used herein refers to selective inhibition and/or stimulation of acetylcholinesterase production, that is an interaction capable of changing the rate of, or stopping, production.

Such selective modulation, i.e. changes in rate of production, can lead for example to (1) changes in neuronal activity, (2) changes in learning and memory, or (3) reduction of AChE in the NMJ, i.e, a reduction in deposition of AChE in the NMJ.

The specific sequence of the AS-ACHE-ODN is determined and tested for efficacy as described herein below. The sequence is selected such that it is targeted to a splice variant of the AChEmRNA that is active/predominant in the central nervous system and/or muscle thereby reducing or eliminating the AS-ODN activity in other tissues. The target sequence is selected so as to be accessible to the AS-ODN and unique to the splice variant in the target tissue. It is possible to select a sequence that while not unique to the splice variant is not accessible to the AS-ODN in other tissues (see Examples). In summary, the AS-ODNs are non-toxic, highly selective for the ACHE gene, operate in a sequence-dependent manner and can be targeted to specific tissue and/or cells.

In an embodiment the antisense oligodeoxynucleotide has one of the following sequences:
5'ACGCTTTCTTGAGGC 3' SEQ ID No:1,
5'GGCACCCTGGGCAGC 3' SEQ ID No:2,
5'GCCAGAGGAGGAGGAGAAGG 3' (hAS-1) SEQ ID No:4,
5'TAGCGTCTACCACCCCTGAC 3' (hAS-2) SEQ ID No:5,
5'CCACGTCCTCCTGCACCGTC 3' (hAS-3) SEQ ID No:6,
5'ATGAACTCGATCTCGTAGCC 3' (hAS-4) SEQ ID No:7,
5'TCTGTGTTATAGCCCAGCCC 3' (hAS-6) SEQ ID No:17,
5'GGCCTGTAACAGTTTATTT 3' (hAS-7) SEQ ID No:18.

SEQ ID No:1 is directed against the human ACHE sequence starting at position 1119 (for numbering of nucleotides see Soreq et al, 1990). SEQ ID No:2 is directed against the human ACHE sequence starting at position 1507. SEQ ID Nos:4–7 and 17–18 are the human equivalent for the mAS sequences tested in Examples 4–8 and correspond to mAS-1–4,6-7 (SEQ ID Nos: 8, 10, 11, 12, 13, 14 respectively). Note that there is little homology between the mAS3 and hAS3 antisense sequence due to the lack of homology between the two species at that position in the sequence. Control hAS sequences were inverse hAS-1 5'GGAAGAGGAGGAGGAGACCG3' (SEQ ID No;19) and inverse hAS-6 5'CCCGACCCGATATTGTGTCT3' (SEQ ID No:20).

The term "oligonucleotide" refers to an oligomer or polymer of nucleotide or nucleoside monomers consisting of naturally occurring bases, sugars and intersugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligonucleotide or only portions thereof may contain the substituted oligomers.

Antisense intervention in the expression of specific genes can be achieved by the use of synthetic antisense oligonucleotide sequences [for recent reports see Lefebvre-d'Hellencourt et al, 1995; Agrawal, 1996; Lev-Lehman et al, 1997]. Antisense oligonucleotide sequences may be short sequences of DNA, typically 15–30 mer but may be as small as 7 mer [Wagner et al, 1996], designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation [Calabretta et al, 1996]. In that case, RNase H will cleave the RNA component of the duplex and can potentially release the AS to further hybridize with additional molecules of the target RNA. An additional mode of action results from the interaction of AS with genomic DNA to form a triple helix which may be transcriptionally inactive.

Antisense induced loss-of-function phenotypes related with cellular development were shown for the glial fibrillary acidic protein (GFAP), for the establishment of tectal plate formation in chick [Galileo et al., 1991] and for the N-myc protein, responsible for the maintenance of cellular heterogeneity in neuroectodermal cultures (ephithelial vs. neuroblastic cells, which differ in their colony forming abilities, tumorigenicity and adherence) [Rosolen et al., 1990; Whitesell et al, 1991]. Antisense oligonucleotide inhibition of basic fibroblast growth factor (bFgF), having mitogenic and angiogenic properties, suppressed 80% of growth in glioma cells [Morrison, 1991] in a saturable and specific manner.

Nuclease resistance, where needed, is provided by any method known in the art that does not substantially interfere with biological activity of the antisense oligodeoxynucleotides as needed for the method of use and delivery [Iyer et al., 1990; Radhakrishnan, et al., 1990; Eckstein, 1985; Spitzer and Eckstein, 1988; Woolf et al., 1990; Shaw et al., 1991]. Modifications that can be made to antisense oligonucleotides in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include preparing 2'-fluoridated, O-methylated, methyl phosphonates, phosphorothioates, phosphorodithioates and morpholino oligomers. In a non-limiting embodiment it is provided by having phosphorothioate bonds linking between the four to six 3'-terminus nucleotide bases. Alternatively, phosphorothioate bonds link all the nucleotide bases. Phosphorothioate antisense oligonucleotides do not normally show significant toxicity at concentrations that are effective and exhibit sufficient pharmacodynamic half-lives in animals [Agarwal et al., 1996] and are nuclease resistant. Alternatively the nuclease resistance can be provided by having a 9 nucleotide loop forming sequence at the 3'-terminus having the nucleotide sequence CGCGAAGCG (SEQ ID No:3). The use of avidin-biotin conjugation reaction can also be used for improved protection of AS-ODNs against serum nuclease degradation [Boado and Pardridge, 1992]. According to this concept the AS-ODN agents are monobiotinylated at their 3'-end. When reacted with avidin, they form tight, nuclease-resistant complexes with 6-fold improved stability over non-conjugated ODNs.

Studies of others have shown extension in vivo of AS-oligodeoxynucleotides [Agarwal et al., 1991]. This process, presumably useful as a scavenging mechanism to remove alien AS-oligonucleotides from the circulation depends on the existence of free 3'-termini in the attached oligonucleotides on which the extension occurs. Therefore partial phosphorothioate, loop protection or biotin-avidin at this important position should be sufficient to ensure stability of these AS-oligodeoxynucleotides.

The present invention also includes all analogues of, or modifications to, an oligonucleotide of the invention that does not substantially affect the function of the oligonucleotide. Such substitutions may be selected, for example, in order to increase cellular uptake or for increased nuclease resistance as is known in the art. The term may also refer to oligonucleotides which contain two or more distinct regions where analogues have been substituted.

The nucleotides can be selected from naturally occurring or synthetically modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, morpholino polymer backbones [U.S. Pat. No. 5,034,506], cyclic backbones, or acyclic backbones, sugar mimetics or any other modification including which can improve the pharmacodynamics properties of the oligonucleotide.

The synthetic nuclease resistant antisense oligodeoxynucleotides of the present invention can be synthesized by any method known in the art. For example, an Applied Biosystems 380B DNA synthesizer can be used. Final purity of the oligonucleotides is determined as is known in the art.

The present invention also discloses a pharmaceutical or medical composition comprising as active ingredient at least one synthetic nuclease resistant antisense oligodeoxynucleotides capable of selectively modulating human acetylcholinesterase production in the central nervous system or neuromuscular junction in a physiologically acceptable carrier or diluent. In one preferred embodiment the synthetic nuclease resistant antisense oligodeoxynucleotide is SEQ ID Nos:1, 2 and 7, however SEQ ID Nos:4–6, 17 and 18 can also be used in the appropriate target.

The present invention also provides a method to restore balanced cholinergic signaling in the central nervous system in patients in need of such treatment such as those with deficits in memory and learing or in stress disorders and Parkinson's. The method comprises administering to a patient in need of such treatment a therapeutically effective amount of at least one of a synthetic nuclease resistant AS-ODN capable of selectively modulating human acetylcholinesterase production in the central nervous system in a physiologically acceptable carrier or diluent. The present invention also provides a method to reduce deposition of acetylcholinesterase in the neuromuscular junction in patients in need of such treatment comprising administering to a patient in need of such treatment a therapeutically effective amount of at least one of a synthetic nuclease resistant AS-ODN capable of selectively modulating human acetylcholinesterase production in the neuromuscular junction in a physiologically acceptable carrier or diluent.

Acceptable carriers, exipients are nontoxic to recipients at the dosages and concentrations employed, and include buffers, such as physiologically acceptable buffers such as phosphate buffered saline, and more generally all suitable carriers known in the art. The compositions may further optionally contain physiologically acceptable additives such as antioxidants; mono- and disaccharides; salt-forming counterions such as sodium and/or nonionic surfactants. Sustained release compositions are also contemplated within the scope of this application. These may include semipermeable polymeric matrices in the form of shaped articles such as films or microcapsules. The antisense oligodeoxynucleotides and compositions of the invention must be sterile. Antisense delivery has also been shown using liposomes [Juliano and Akhtar, 1992].

In one embodiment the synthetic nuclease resistant antisense oligodeoxynucleotide is SEQ ID Nos:1, 2, 6 and 7, however SEQ ID Nos:4–5, 17 and 18 can also be used in the appropriate target.

An important feature of the present nuclease resistant antisense oligodeoxynucleotide invention is that they can be administered by simple subcutaneous, intramuscular, intravenous or intraperitoneal injection and that their effects last for at least several weeks. The limited toxicity of the AS-ODNs of the present invention is of particular importance for their therapeutical uses.

The AS-ODN is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to changes in levels of AChE in the CNS or neuromuscular junction, or improvement or elimination of symptoms and other indicators as are selected as appropriate measures by those skilled in the art.

For specific delivery within the CNS intrathecal delivery can be used with, for example, an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood-brain barrier can be administered. [Betz et al., 1994; Brem et al., 1993]. Such formulations can take advantage of methods now available to produce chimeric molecules in which the present invention is coupled to a brain transport vector allowing transportation across the barrier [Pardridge, et al., 1992; Pardridge, 1992; Bickel, et al., 1993]. Further, Applicant's in a co-pending application U.S. patent application Ser. No. 08/975,084 filed Nov. 20, 1997 assigned to the same assignee and incorporated in its entirety herein by reference have demonstrated that a stress-mimicking inducing agent or treatment will open the barrier such as the ACHE-I4 readthrough splice variant or the I4 peptide or adrenaline or atropine.

For modulating the production and therefore deposition of AChE at the neuromuscular junction, AS-ODNs which target the muscle form are used. In general, being hydrophobic antisense oligonucleotides interact well with phospholipid membranes [Akhter et al., 1991]. Following their interaction with the cellular plasma membrane, they are actively transported into living cells [Loke et al., 1989], in a saturable mechanism predicted to involve specific receptors [Yakubov et al., 1989]. Therefore, AS-ODN are available to the muscle cells which produce AChE that is deposited (transported, released to) the neuromuscular junction.

As with any drug, testing the potential therapeutic utility of antisense oligonucleotides targeted against acetylcholinesterase requires an appropriate model, either in vivo, ex vivo or in vitro. Since mice do not naturally develop a disease resembling human dementia, Applicants have generated a unique transgenic mouse model for Alzheimer's Disease to serve this purpose [Beeri et al., 1995 and co-pending U.S. patent application Ser. No. 08/370,156 assigned to the same assignee and incorporated in its entirety herein by reference]. These genetically engineered mice overproduce human acetylcholinesterase in cholinergic brain cells. Excess acetylcholinesterase in brain cells induce acetylcholine shortages similar to those assumed to promote the cognitive dysfunction associated with Alzheimer's Disease. And, indeed, Applicants transgenic mice display age-dependent deterioration in cognitive performance as initially measured by a standardized swimming test for spatial learning and memory, a social recognition test as set forth in Example 7 herein below and a taste aversion test. Since the excess acetylcholinesterase in the brains of these mice is derived from human DNA, it is susceptible to antisense oligonucleotides targeted against the human acetylcholinesterase gene. This animal system and brain slices derived thereof, therefore provides the ability to test anti-acetylcholinesterase antisense technology by in vivo, ex vivo and in vitro means to restore balanced cholinergic signaling in the brain and thereby relieve some of the impaired cognitive function from which Alzheimer's Disease patients suffer and to test the efficacy of treatment initiated at pre-symptomatic stages. In general, initial screening for efficacy occurs ex vivo or in vitro, preferably in brain slices. Following this screening the AS-ODN is tested in the hACHE transgenic mice for efficacy. Suitable candidates for human testing are thereby determined. This model system also responds to Tacrine in the same manner as humans (see Examples) thereby also supporting its use as a model system for testing AS-ODNs.

For testing of AS-ODN in myasthenic animals, the Experimental Autoimmune Myasthenia Gravis model is available. Further, Applicants have shown [Andres et al, 1997] via in vivo behavioral tests (rope-gripping) and in situ histology (synapses have an MG-like structure) a mimicking model for MG in transgenic mice that overexpress AChE which can be used in testing new AS-ODNs.

Applicants have established protocols for in vivo administration of oligonucleotides using intravenous, intraperitoneal, and direct intracerebroventricular (i.c.v.) routes. Results show the efficacy of nuclease resistant antisense oligonucleotides in reducing AChE catalytic activity in brain tissue of transgenic mice. These studies provide the basis for testing and defining therapeutically useful forms and doses of oligonucleotides in vivo.

As shown in the Examples, AS-ACHE-ODNs have been produced and injected which are targeted against both human and mouse AChEmRNA (see Tables I and II). AS-ODNs were nuclease resistant as indicated.

Figure 3:
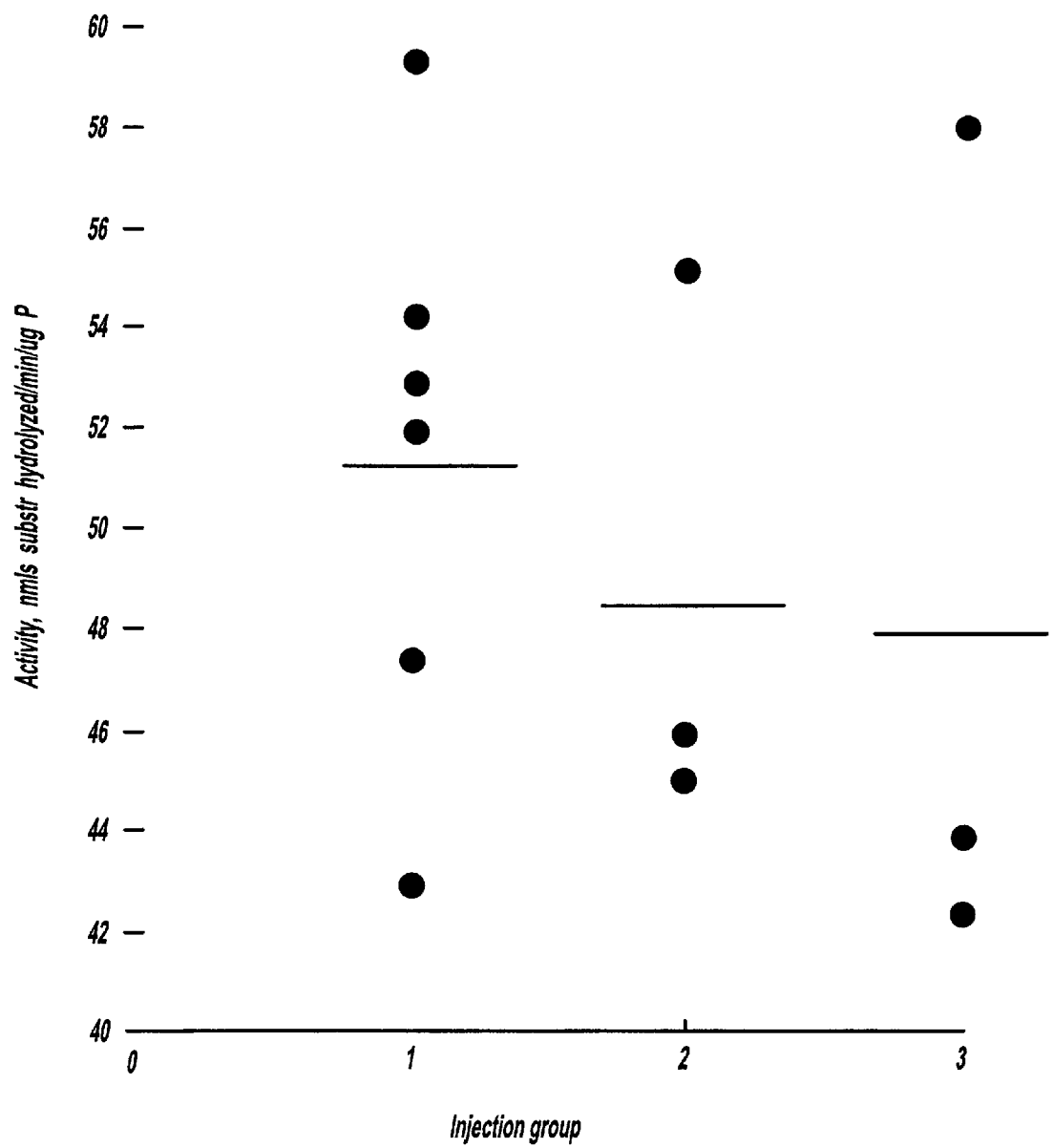
FIG. 3 is a graph showing that antisense oligonucleotides injected i.c.v. gives a reduction in AChE catalytic activity in subcortical regions. Each circle represents the AChE activity measured in the subcortical region of a single injected mouse. The column of buffer-injected mice represents data from two independent experiments performed on age-matched mice. The average activity calculated for each group is indicated by a horizontal line.

No acute toxic effects were observed in any AS-ODN treated human transgenic mouse and behavior appeared normal in all treated animals. AS-ODN targeted against hAChEmRNA resulted in diminished levels of both hAChE- and mAChE mRNAs (FIG. 2) and dramatically reduced protein levels in one of two animals. AS-ODN against mAChEmRNA resulted in a 3 cycle delay in appearance of RT-PCR product in one animal (approx 8-fold reduction in mRNA). When 100 pmole (approx 1 ug) AS-ODN against hAChE- or mAChE- mRNA was delivered i.c.v. to 15 day old mice, 2 of 3 mice in each group displayed total AChE activities >1 S.D. below the mean activity measured in buffer injected animals 40 hours post injection (FIG. 3).

Figure 4A:
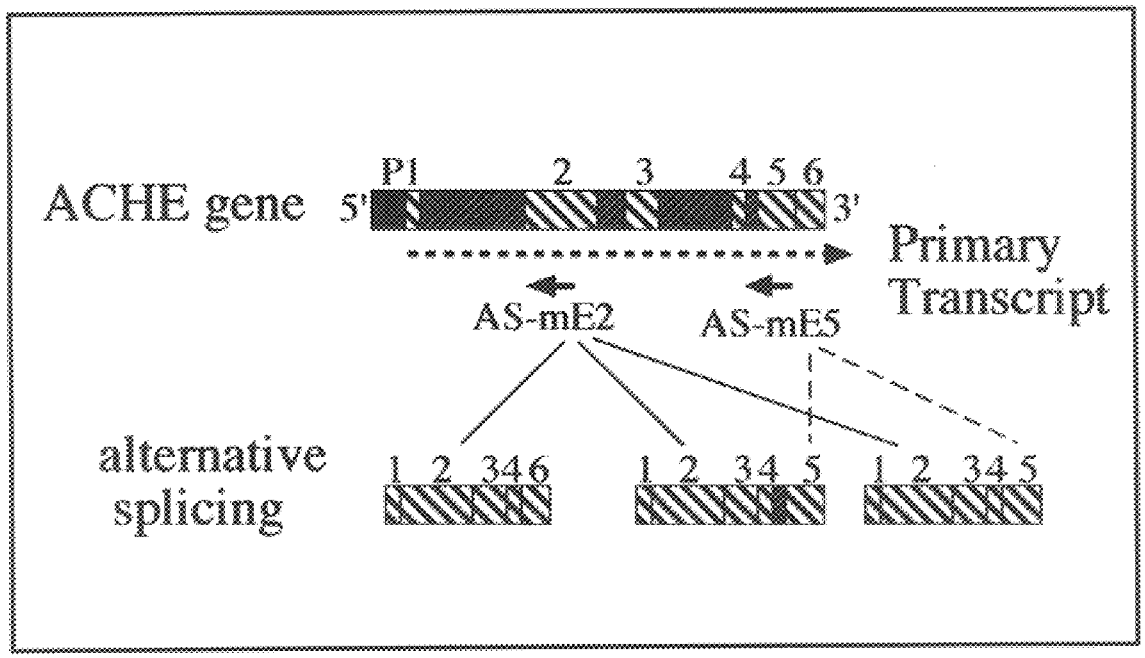
FIGS. 4A–B demonstrates the in vivo antisense suppression of ACHEmRNA wherein FIG. 4A schematically presents the mouse ACHE gene with its promoter (P), 6 exons (numbered 1–6) and 4 introns. Alternative splicing yields 3 variant mRNA transcripts that encode polypeptides differing in their C-terminal peptide sequences.
Figure 11:
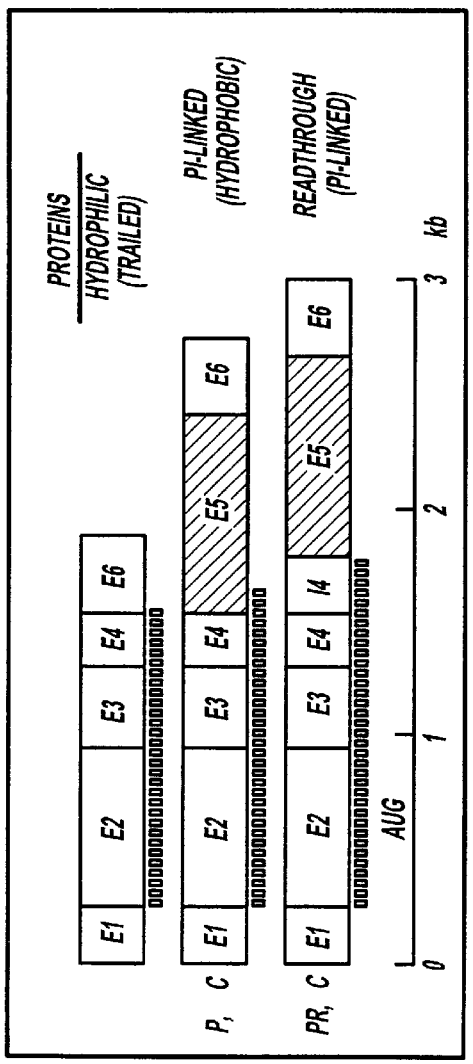
FIG. 11 is a is a schematic diagram of the three splice variants of AChE.
Figure 12:
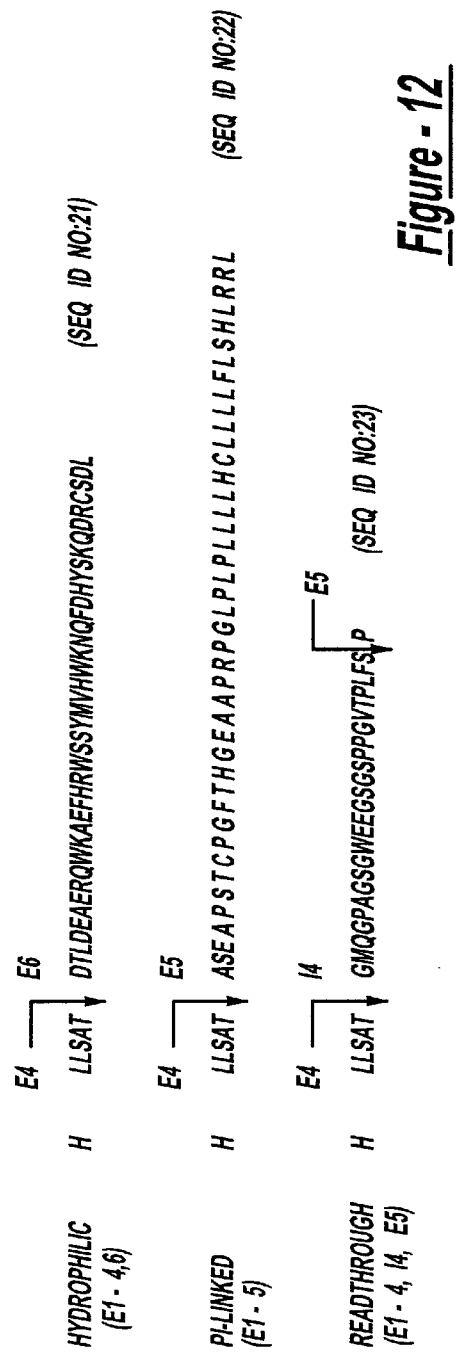
FIG. 12 shows the amino acid sequences of human (H) AChE variants from the end of E4 to the end of the protein in the three variants, E1–4,6 (SEQ ID No:21), E1–5 (SEQ ID No:22), E1–4-I4-E5 (readthrough; SEQ ID No:23).

In designing AS-ODNs for ACHEmRNA in target cells it is necessary to define which of the three alternative transcripts expressed in mammals is present in these cells. PCR amplification using primers selective for each of the transcripts determines which are present and in what intensity. In general the transcript with the highest intensity in the target tissue is selected. As shown in the Examples there are tissue differences (see FIGS. 4 and 5). As previously discussed the dominant central nervous system and muscle AChE (AChE-T) found in the neuromuscular junction (NMJ) is encoded by an mRNA carrying exon E1 and the invariant coding exons E2, E3, and E4 spliced to alternative exon E6 [Li et al., 1991; Ben Aziz-Aloya et al., 1993]. As shown in the Examples, it is possible that an AS targeted to a specific Exon will target both pre- and post-splice AChEmRNA. In order to specifically target the post-splice AChEmRNA the unique splice junction of the three forms can be targeted by the antisense (FIGS. 11–12) after splicing has occurred. A 20 mer AS-ODN is preferred but other lengths are used that are complementary to the unique sequence at the splice junction. The antisense seqeunces generally extend 10 nucleotides on either side of the junction, but other ranges on each side can be used as long as they define the unique splice junction sequence. In an embodiment an AS-ODN targeted against the E4–E6 junction sequence (FIG. 12) will be generally specific for the central nervous system and neuromuscular junction form (AChE-T) as shown in the Examples.

Interestingly, as described herein the mAS-ODNs, except mAS6 and mAS7, were targeted against translationable sequences included in the open reading frame of ACHEmRNA. mAS7, targeted to the 3'-region of exon 6, was significantly less effective than those designed against the sequence common to all alternatively-spliced ACHEmRNA transcripts. This is not a general rule; on the contrary, AS-ODNs against 3'- regions in other mRNAs were shown to effectively induce destruction of the entire mRNA sequence [e.g. Bennet et al., 1994]. However, mammalian ACHEmRNA is especially rich in G,C base pairs (67% in human ACHE, Soreq et al., 1990). Therefore, it is likely to be tightly folded. Since a truncated human ACHEmRNA bearing only exons 2, 3 and 4 was found to be translatable in Xenopus embryos [Seidman et al., 1997], it is possible that E6-ACHEmRNA is so tightly folded that RNaseH action on its 3'-exon does not lead to destruction of exons 2, 3 and 4, leaving an mRNA which encodes a catalytically active, C-terminally truncated protein. Therefore, an AS directed against the E4-E6 junction sequence will be effected where one directed against the 3' region may not be.

The above discussion provides a factual basis for the use of AS-ODN. The methods used with and the utility of the present invention can be shown by the following non-limiting examples and accompanying figures.

EXAMPLES

General Methods

General Methods in Molecular Biology

Standard molecular biology techniques known in the art and not specifically described were generally followed as in Sambrook et al., *Molecular Cloning: A Laboratory Manual,* Cold Springs Harbor Laboratory, New York (1989, 1992), and in Ausubel et al., *Current Protocols in Molecular Biology,* John Wiley and Sons, Baltimore, Md. (1989). Polymerase chain reaction (PCR) was carried out generally as in *PCR Protocols: A Guide To Methods And Applications,* Academic Press, San Diego, Calif. (1990).

Reactions and manipulations involving other nucleic acid techniques, unless stated otherwise, were performed as generally described in Sambrook et al., 1989, *Molecular Cloning: A Laboratory Manual,* Cold Spring Harbor Laboratory Press, and methodology as set forth in U.S. Pat. Nos. 4,666,828; 4,683,202; 4,801,531; 5,192,659 and 5,272,057 and incorporated herein by reference.

Synthesis of Antisense Oligodeoxynucleotides

Oligodeoxynucleotides were synthesized on an Applied Biosystems 380B DNA synthesizer using phosphoramidites from the same company according to the manufacturer's instructions. They were purified by reverse phase HPLC on a Waters dual pump 6000A system in combination with a Waters automated gradient controller and a model 481 UV spectrophotometer operated at 260 nm with the 5'-protecting dimethoxytrityl group still attached to the oligodeoxynucleotides. This was removed by standard treatment with 80% aqueous acetic acid. The oligodeoxynucleotides obtained were checked for purity again by HPLC.

For nuclease resistance where phosphorothioate groups where incorporated, the oxidation step employing iodine was replaced by reaction with 3H-1,2-benzodithiol-3-one 1, 1-dioxide [Iyer et al., 1990]. This treatment protects the oligodeoxynucleotides against nuclease [Eckstein, 1985; Spitzer and Eckstein, 1988] and prolongs their duration in vivo [Woolf et al., 1990; Shaw et al., 1991]. Wherever partial protection was required, reaction with 3H-1,2-benzodithiol-3-one 1,1-dioxide was performed for the first three steps only, after which regular synthesis was continued. The resultant partially protected oligodeoxynucleotides were therefore blocked by phosphorothioate groups only in the last three internucleotidic bonds at their 3'-terminus.

For inclusion of a loop, the synthesis of the oligodeoxynucleotide was extended at the 3' end to include SEQ ID No:3.

The antisense oligodeoxynucleotides were kept in 4 mM concentration at −20° C. and were diluted in phosphate buffered saline (PBS) prior to their administration to mice.

Example 1

Summary of Prior Work with AS-ACHE-ODN in the Hematopoietic System

Because of its unique properties, the hematopoietic system is particularly well suited for antisense intervention with multiple cellular and molecular processes. The rapid proliferation and short half life of hematopoietic cells as well as the efficient uptake and accessibility of AS-ODNs in them are among the reasons for these efficient effects of AS-ODNs in hematopoietic cells [Calabretta et al., 1996; Gerwirz et al, 1993].

To examine the role of AChE in controlling hematopoietic composition in general and megakaryocytic (MK) development in particular, mature female mice were treated in vivo with phosphorothioate AS-ACHE. To monitor the effects of this treatment, bone marrow differential cell counts were combined with a kinetic follow-up of polymerase chain reaction products (RNA-PCR) in different tissues [Lev-Lehman et al., 1994]. In situ hybridization with $^{35}$S-labeled ACHE and BCHE cRNA probes, followed by computerized quantification of the hybridization data was used to associate mRNA levels with specific cell types. The RNA-PCR analysis demonstrated an apparently total abolition of ACHE mRNA at 12 days post-treatment, when lymphocyte and erythroid fractions were drastically reduced in the bone marrow of treated mice. This implicates ACHE in the development of both lymphocytes and erythrocytes, two cell lineages expressing this enzyme as well as showing the effectiveness of AS-ODN treatment.

Because of their small numbers and longevity, it would not be informative to evaluate differences in the MK fraction at day 12 since part of the MK would still represent cells from the pre-treatment period. However, the secondary decrease in actin mRNA in the bone marrow, where MK are replete with this mRNA species was taken as an indication of decrease in MK as well. As MK and erythroid cells are considered to share a common progenitor, these findings further suggest that these progenitors are similarly affected by the AS-ACHE treatment.

Lymph nodes were selected as an additional tissue for the RT-PCR experiments since this tissue is subject to a continuous replacement, similarly to bone marrow cells. The drastic decrease in lymph node ACHE mRNA levels 12 days post-treatment demonstrated efficient tissue distribution of the administered AS-ACHE oligo.

These findings demonstrate transient changes in hematopoietic cell composition following AS-ACHE treatment, and in particular—increased myeloid fraction [Patinkin, et al., 1990, 1994; Lev-Lehman et al., 1994].

The in vivo effects of AS-ACHE oligonucleotides in increasing the myeloid fraction in bone marrow as discussed herein above, could reflect expansion of progenitors, which could first be evident by an increase in the faster-developing myeloid cells. Additionally or alternatively, it could be due to enhanced myeloidogenesis or suppressed erythropoiesis. To distinguish between these possibilities, and to more closely investigate the function of the ACHE gene in hematopoiesis, AS-ACHE was administered ex-vivo to primary hematopoietic cells. Its effects on gene expression, expansion of progenitors, and differential cell composition on mouse CFU-MK and CFU-GEMM colonies was examined [Soreq et al., 1994]. These experiments, as well, resulted in an increase in the fraction of myeloid cells, reflecting both expansion of progenitors and increase in the development of their progeny cells [Soreq et al., 1994].

The ex vivo experiments, using primary murine bone marrow cultures, provide an additional advantage over the in vivo ones in that the effects of growth factors can be studied individually. For example, in such primary cultures interleukin 3 (IL-3) induces expansion of a fraction of the existing pluripotent stem cells into multipotent progenitors, which can differentiate into megakaryocyte colony-forming units (CFU-MK) composed of granulocytes, megakaryocytes, and macrophages [Patinkin et al., 1990; Lapidot-Lifson et al., 1992]. Addition of erythropoietin and transferrin to IL-3 and longer incubation times induce CFU-GEMM colonies, which contain granulocytes, erythroid cells, megakaryocytes, and macrophages. This implies that colony counts reflect expansion and survival of progenitors that have given rise to progeny, whereas cell numbers reflect proliferation rates, and differential cell compositions demonstrate which cell lineages developed and which were programmed to die. Interference with expression of hematopoietically important genes by AS-ODN agents [Stein and Cheng, 1993] can conceivably alter any or all of the characteristics of these cultures, and as applicants have shown AS-ODNs targeted to cdc kinases [Lapidot-Lifson et al., 1992] and to the ACHE-related gene BCHE [Lapidot-Lifson et al., 1989; Soreq and Zakut, 1993], impair megakaryocytopoiesis in CFU-MK colonies [Lapidot-Lifson et al., 1992; Patinkin et al., 1994; Soreq et al., 1994].

Example 2

Summary of Prior Work with AS-BCHE-ODN in the Hematopoietic System

The role of BuChE in hematopoiesis was studied by comparing the effects of AS-BCHE ODN administered to primary murine bone marrow cultures to those observed for AS-ACHE ODNs. The findings demonstrated certain enhancement in myeloid cell fractions and corresponding suppression of the megakaryocyte fractions in both CFU-MK and CFU-GEMM cultures administered with AS-BCHE ODNs. This erythropoietin-independent effect was sequence-dependent and not associated with general apoptotic changes. Complementary in vivo studies revealed continuation of the antisense-inducted destruction of BCHEmRNA for over 2 weeks, no effect on megakaryocytes survival and ex-vivo suppression of CFU-MK expansion capacity following the in vivo treatment. Thus, AS-ACHE and AS-BCHE agents can be expected to exert similar effects on megakaryocytopoiesis although they do not cross-react with each other's target.

To avoid non-specific cytotoxicity of the oligonucleotides, partial phosphorothioated was used to protect the relevant oligos, replacing only the three 3'-terminal internucleotidic bonds with phosphorothioate groups [Ehrlich et al., 1994]. Demonstration of a non-disturbed apoptotic index in experimental cell cultures, evidenced in unchanged ladders of fragmented DNA, indicated that the studied effects did not result from non-specific induction of programmed cell death. This, in turn, suggests that the increase in myeloid cell fraction was primarily due to selective destruction of the target BCHEmRNA and the AS-ODNs.

Other experiments in this series demonstrated non-sequence dependent effects of AS-ODE agents over hematopoiesis ex vivo. In both CFU-MK and CFU-GEMM cultures, partially protected AS-BCFE but not the sense oriented sequence S-BCHE enhanced myeloid and granulocyte counts while reducing the fraction of early megakaryocytes. However, in CFU-MK cultures, sequence-independent effects of the employed S-BCHE oligo increased the variability in colony counts. In contrast, the variability in CFU-GEMM colony counts was reduced under AS-BCHE treatment, together with suppression of megakaryocytes. These observations confirmed and extended applicants' previous findings [Patinkin et al., 1990; Lapidot-Lifson et al., 1992; Lev-Lehman et al., 1994; Ehrlich et al., 1994] while demonstrating that the hematopoietic diversion induced by AS-BCHE from megakaryopoietic toward the myeloidocenic lineages is erythropoietin-independent, involves increases in myeloid proliferation and occurs also under in vivo conditions. These findings also indicate that CFU-GEMM progenitors respond to AS-BCHE in a less variable manner than CFU-MK progenitors. Individual progenitor cells may therefore be expected to respond to specific AS-ODN agents with different levels of variability, dependent both on the oligo and on the cell type in question.

Similar to the effects of AS-ACRE, the suppression of megakaryocytopoiesis by AS-BCHE occurred throughout the dose-response curve of CFU-GEMM.

The long-term in vivo-ex vivo duration of AS-BCHE effects is of special interest. It indicates that the AS-BCHE-induced destruction of BCHEmRNA in young promegakaryocytes was capable of reducing development of these cells for at least two weeks and demonstrates that no feedback responses occurred to compensate for BCHE suppression and retrieve normal production of megakaryocytes.

In general, the AS-BCHE effects were limited as compared with the distinct effects caused by ex-vivo and in vivo treatment with the parallel AS-ACHE ODNs blocking ACHE expression. Like AS-BCHE, AS-ACHE also suppresses megakaryocyte formation. However, unlike AS-BCHE, it also suppresses erythropoiesis ex-vivo and in vivo [Lev-Lehman et al., 1994; Soreq et al., 1994], suggesting that acetylcholinesterase participates in the erythropoietic process as well. Moreover, AS-ACHE, but not AS-BCHE induces a dramatic ex vivo expansion of CFU-GEMM colony production and cell proliferation and reduces apoptosis in CFU-GEMM primary bone marrow cultures [Soreq et al., 1994]. These differences reveal distinctions between the role(s) played by the two cholinesterases in mammalian hematopoiesis. Development of both novel anticholinesterases and AS-ODN agents targeted to these mRNAs as set forth in the present application take into consideration the hematopoietic involvement of the protein products of these mRNAs as well as their distinct role in the hematopoietic process.

Example 3

AS-ODN in Mice at the Neuromuscular Junction

Another prominent site for ChE activities is the neuromuscular junction, where ChEs control the cholinergic innervation of motor functioning. Therefore, it would be important to ensure that only the desired tissue will be affected under systemic administration of a specific AS-ODN.

In vivo administration of an AS-ACHE oligo altered hematopoiesis in injected mice [Lev-Lehman et al., 1994] as described in Examples 1 and 2 herein above. In order to apply this technology to an extended in vivo use, applicants asked whether injection of certain AS-ODNs always affect the target mRNA in other tissues as well (FIG. 4).

Five week old, female, white Sabra mice were injected (i.p.) once per day for 3 days with 0.2 ml PBS or with PBS containing 3'-terminally phosphorothioated oligodeoxynucleotides (5 µg/g body weight) targeted against the mouse ACHE gene. Two antisense (AS) oligonucleotides were used, one targeted against the common exon E2 (mE2; mouse E2; SEQ ID No:8) or the alternative hematopoietic exon E5 (mE5; mouse E5; SEQ ID No:9) compared with those of sense (S) oligos based on the homologous human ACHE gene sequence or sham injections with PBS. β-actin mRNA served as a control for non-specific effects on transcription. Mice were sacrificed 24 hours following the last injection and total RNA prepared from muscle and bone marrow (BM). Semi-quantitative RT-PCR was performed on 100 ng samples of RNA using a primer pair (+1361/−1844) anchored in mouse ACHE gene exons E4 (+) and E6 (−). Samples were removed for analysis every 3 cycles between cycles 24 and 33. Both AS-mE2 and AS-mE5 exert specific reduction of E6-containing ACHEmRNA in bone marrow but not muscle at the administered doses while actin mRNA was unaffected by any treatment.

The AS-mE2 ODN potentially hybridizes to the three alternative splicing forms of ACHEmRNA transcripts that encode polypeptides differing in their C-terminal peptide sequences (FIG. 4A): the "synaptic form" containing exons E2–E3–E4–E6, the "readthrough form" (containing exons E2–E3–E4–I4–E5 and the "hematopoietic form" containing exons E2–E3–E4–E5. AS-mE2 (an antisense sequence selected in the E2 exon) was therefore expected to be highly efficient in all of the tissues where AChE is expressed. On the other hand, AS-mE5 (an antisense sequence selected in the E5 exon, SEQ ID No:9) should only be able to hybridize to the last two forms, which limits its potential efficacy in the CNS.

Figure 4B:
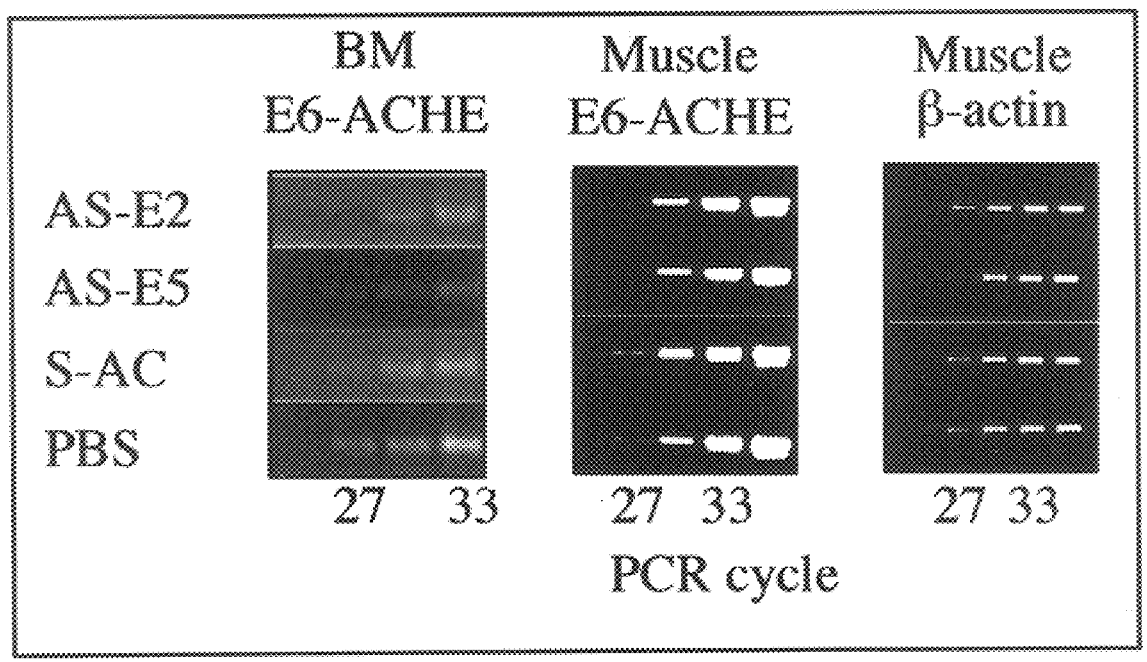
Figure 5A:
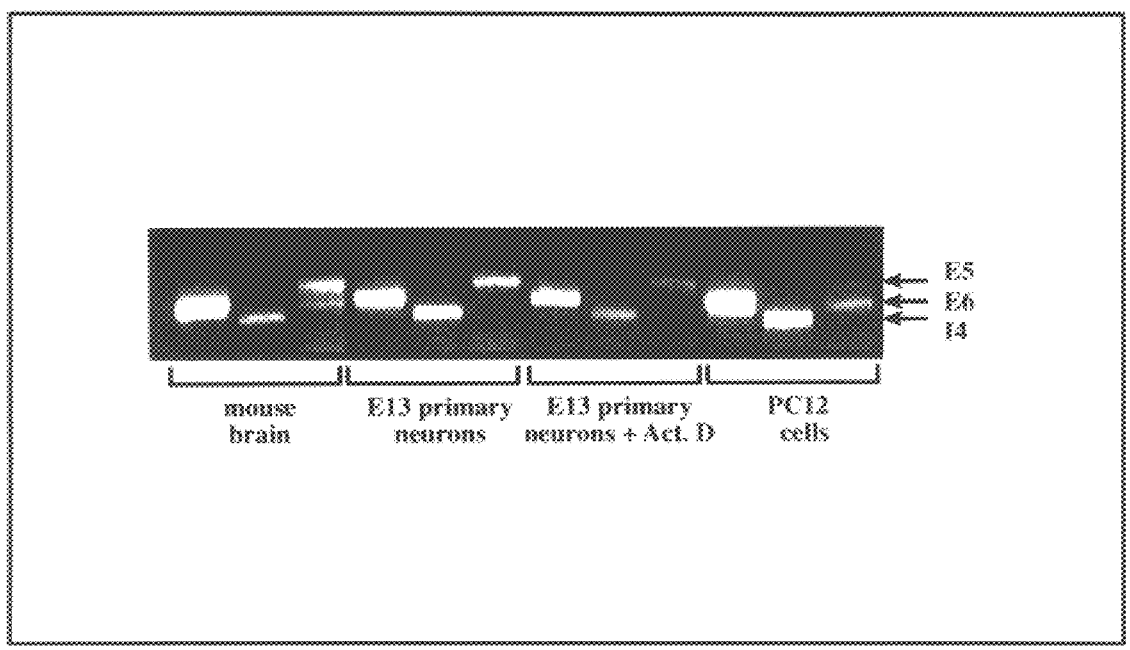
Figure 5B:
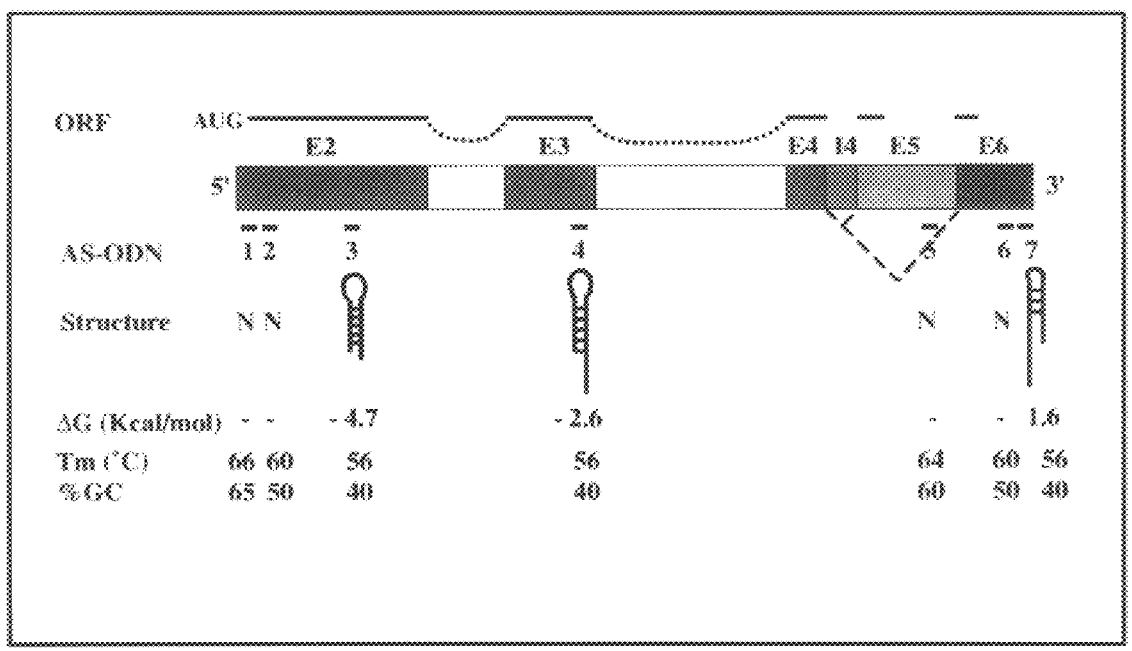

RNA-based PCR amplification (RT-PCR) was performed on RNA extracted from bone marrow (BM), muscle and brain of the injected animals with different PCR primers. To test whether these AS-ODNs exert non-specific toxic effects on total RNA degradation RT-PCR with primers for β-actin (for primer sequences see Lev-Lehman et al., 1994) was employed. An effective decrease in the level of E6-ACHE occurred in BM but not brain after AS-mE2 ODN injection as compared with a subtle decrease in muscle (FIG. 4B). A more limited decrease in E6-ACHE mRNA was observed in muscle and bone marrow, hut not brain, of animals treated with the AS-mE5 ODN. This could reflect limitations in access into the brain as well as hybridization with the primary transcript of AChEmRNA in the nucleus of the muscle and cells of the bone marrow, leading to its degradation or inhibition of the splicing process and transport into the cytoplasm. These results are in agreement with the already discussed higher susceptibility of bone marrow to AS-ODN. Thus, in vivo administration of AS-ODN does not necessarily cause the same effect in different tissues expressing the targeted proteins. This allows the design of specific AS-ACHE-ODNs to be targeted to specific tissues.

Example 4

In Vitro Testing of AS-ODNs

The PC12 cell line, derived from rat phaechromocytoma cells, is a well-established model for studying vertebrate cholinergic neurons which can be induced to differentiate by nerve growth factor (NGF). NGF treatment is shown to arrest the proliferation of PC12 cells, change their gene expression pattern [Lee et al., 1995] and induce their differentiation toward a cholinergic phenotype with increased AChE activity and neurite-like processes [Greene and Tischler, 1976; Tao-Chang et al., 1995]. Therefore, NGF-pre-treated PC12 cells will differ significantly from non-treated ones in their membrane properties, cytoarchitecture and levels of ACHEmRNA.

These cells can be used as a model to screen for the neurotoxicity of AS-ODNs which have been protected against nucleolytic degradation and to determine if there is differences in responses depending on the stage of differentiation of the cells. The series of AS-ACHE ODNs was tested on PC12 cells before, during and after induction of differentiation by NGF.

Materials and Methods

Cell Lines

Rat phaechromocytoma PC12 cells were provided by Dr. R. Stein, Tel-Aviv University. Cells are grown in Dulbecco's modified Eagle's medium supplemented with 8% fetal calf serum, 8% horse serum, 2 mM glutamine, 100 U/ml penicillin and 0.1 mg/ml streptomycin. Cells are kept at 37° C. in a fully humidified atmosphere at 5% carbon dioxide. For differentiation, 50 ng/ml NGF (Alomone Laboratories, Jerusalem, Israel) is added. All tissue culture reagents are from Biological Industries (Beit Haemek, Israel).

Primary Cultures

Primary mouse neuronal cultures are prepared from embryonic (e14) mouse (Balb/C) whole brains. Brains are removed and cells mechanically dissociated by being drawn through a Pasteur pipette. Cells are plated in serum-free medium ($2.5 \times 10^6$ cells/ml) in 24-well (1 ml per well) Costar (Cambridge, Mass.) culture dishes coated successively with poly-L-ornithine and culture medium containing 10% fetal calf serum [Weiss et al., 1986] Wherever mentioned, Actinomycin D is added for 72 hours at 0.5 µg/ml.

Oligonucleotides

The AS-ODNS were synthesized by Microsynth (Balgach, Switzerland). The ODNs were 20 nucleotides in length with the last three 3' internucleotidic linages phosphorothioated. The seven ODNs tested were targeted towards various sites along the mouse ACHEmRNA chain taking into account exon splice variables (SEQ ID Nos:8–14). The most abundant mature transcript in brain is one in which exon 4 is spliced to exon 6. The mAS-ODNs had the following sequences:

Experimental Sequences:

| | | |
|---|---|---|
| mAS1 (ASmE2) | 5'-GGGAGAGGAGGAGGAAGAGG-3' | SEQ ID No:8 |
| mAS2 | 5'-TAGCATCCAACACTCCTGAC-3' | SEQ ID No:10 |
| mAS3 | 5'-CTGCAATATTTTCTTGCACC-3' | SEQ ID No:11 |
| mAS4 | 5'-ATGAACTCGATTTCATAGCC-3' | SEQ ID No:12 |
| mAS5 (ASmE5) | 5'-AGAGGAGGGACAGGGCTAAG-3' | SEQ ID No:9 |
| mAS6 | 5'-GTCGTATTATATCCCAGCCC-3' | SEQ ID No:13 |
| mAS7 | 5'-GTGGCTGTAACAGTTTATTG-3' | SEQ ID No:14 |

Control Sequences

| | | |
|---|---|---|
| MASB | 5'-GACTTTGCTATGCAT-3' | SEQ ID No:15 |
| mI-AS5 | 5'-GAATCGGGACAGGGAGGAGA-3' | SEQ ID No:16 | mAS1 (position in neuronal mouse transcript 70) and mAS2 (880) are in close proximity to the translation initiation site in exon 2. mAS3 (658) and mAS4 (1454) are located in exons 2 and 3 common to all the splice variables. mAS5 (234) is targeted to exon 5; this particular ODN should hybridize with the alternative E5 ACHEmRNA, yet not with mature E6 transcript. mAS6 (1932; SEQ ID No:13) and mAS7 (2068; SEQ ID No:17) were designed to hybridize with exon 6. No mAS-ODN was designed for I4, since its sequence is the most variable among mammals [Karpel et al., 1994]. All mAS-ODNs, except mAS6 and mAS7, were targeted against translationable sequences included in the open reading frame of ACHEmRNA. (see FIG. 5B for schematic position of AS-ODN in gene)

Antisense Treatment

PC12 cells are grown to 50% confluence (approx. 105 cells per well) in 96-well Nunclon™ (Nunc, Roskilde, Denmark) microtiter plates. Following 24 hours in culture, fetal calf and horse sera are reduced to 2% each and either 1 or 10 μM ODN added to the culture medium for an additional 24 hours. In certain experiments, Lipofectamine™ was added together with the ODN essentially as instructed by the producer (GicoBRL, Gaithersburg, Md.), except that 1 μM ODN is used together with 2.5μl Lipofectamine™ per well.

Colorimetric Measurements

Figure 6A:
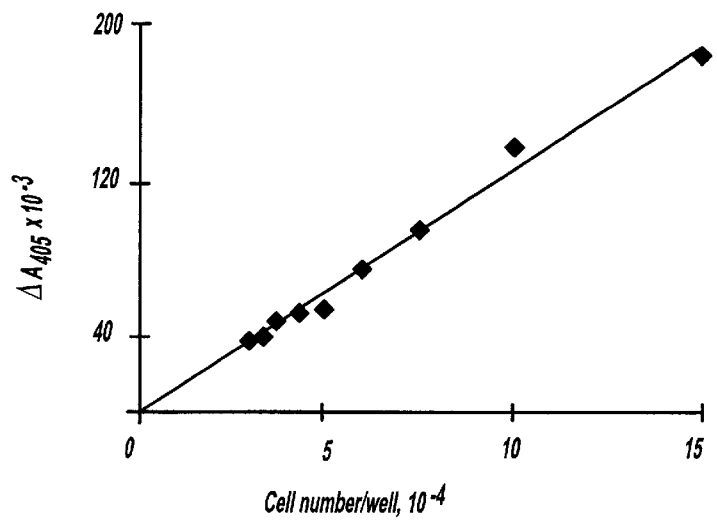

Following ODN treatment, cells are washed once with phosphate-buffered saline and lysed with 1% Titon X-100 in 200 μl of 100 mM phosphate buffer, pH 7.4 containing 0.5 mM dithio-bis-nitrobenzoic acid (DTNB) for 20 minutes. Washing removes dead cells, which do not adhere to the well surface. To evaluate cell survival after AS-ODN treatment, the content of free thiol groups in these cells is measured. Such groups react with DTNB to yield the yellow anion 5-thio-2-nitrobenzoate, which can be quantified in the same microtiter wells by absorption at 405 nm ($\epsilon_{405}$=13,600 M$^{-1}$ cm$^{-1}$). Such absorbance was found to be proportional to the concentration of cells within each well and served as a measure of cell number (FIG. 6A). AChE activity was subsequently measured following the addition of 1 mM acetylthiocholine to the DTNB solution in the same wells, using an adaptation of Ellman's assay [Ellman et al., 1961] for use with 96-well microtiter plates [Seidman et al., 1994]. For testing AS-ODN-AChE interactions, similar assays were performed with highly purified recombinant human AChE (Sigma Chemical Co., St. Louis, Mo., USA) incubated with the noted quantities of ODNs.

RNA Extraction and PCR

Total RNA was extracted from whole brain, embryonic brain neurons and PC12 cells, using RNazol™ (Biotecx Laboratories, Inc., Houston, Tex.) as detailed elsewhere [Karpel et al., 1994]. Reverse transcription followed by PCR amplification was performed as described by Karpel et al., 1994.

Kinetics of accumulation of RT-PCR products is studied by removal of 12 μl aliquots at 6 alternate cycles in the PCR procedure. Collected DNA is electrophoresed on ethidium bromide stained agarose gels. UV images of these gels are digitized using a charge coupled device (CCD) camera. The intensity of fluorescence is quantified using the program IpLab Spectrum (Signal Analytics, Vienna, Va., USA), for quadruple PCR reactions. Resultant values are plotted as percent of the maximal intensity obtained at a time point when the control set of PCR reactions reaches a plateau. Under ideal conditions, fluorescence intensity should increase exponentially throughout this kinetic follow-up, with the vertical separation between individual curves dependent on the initial quantity of the examined mRNA. Linear regression analysis of relative fluorescence units vs. Cycle number should therefore yield an estimate of the amount of the template originally present. In cases where selective mRNA destruction took place, the levels of the target mRNA, but not an irrelevant control mRNA should show vertical shifts in the kinetic accumulation curves, reflected in different intercepts with the y axis.

Results

The three alternative ACHEmRNA splice variants are present in P12 cells with E6>I4>E5 (FIG. 5A), a pattern similar to that found in both embryonic mouse brain neurons and adult mouse brain.

In the experiments reported herein, the AS-ODNs were protected by 3'-phosphorothioation. Since the original ACHE transcript may be alternatively spliced to produce three different mRNAs, in this study the efficacy of AS-ODNs targeted the different mature mRNA isoforms in suppression of the production of AChE in differentiated (NGF-treated) and non-differentiated cells was undertaken.

Three different administration protocols were used: non-differentiated PC12 cells were treated with 1 μM AS-ODN alone or with NGF for 24 hours, or NGF-induced differentiation was allowed to proceed for 24 hours before being exposed for a second 24 hours to the AS-ODN.

Figure 6B:
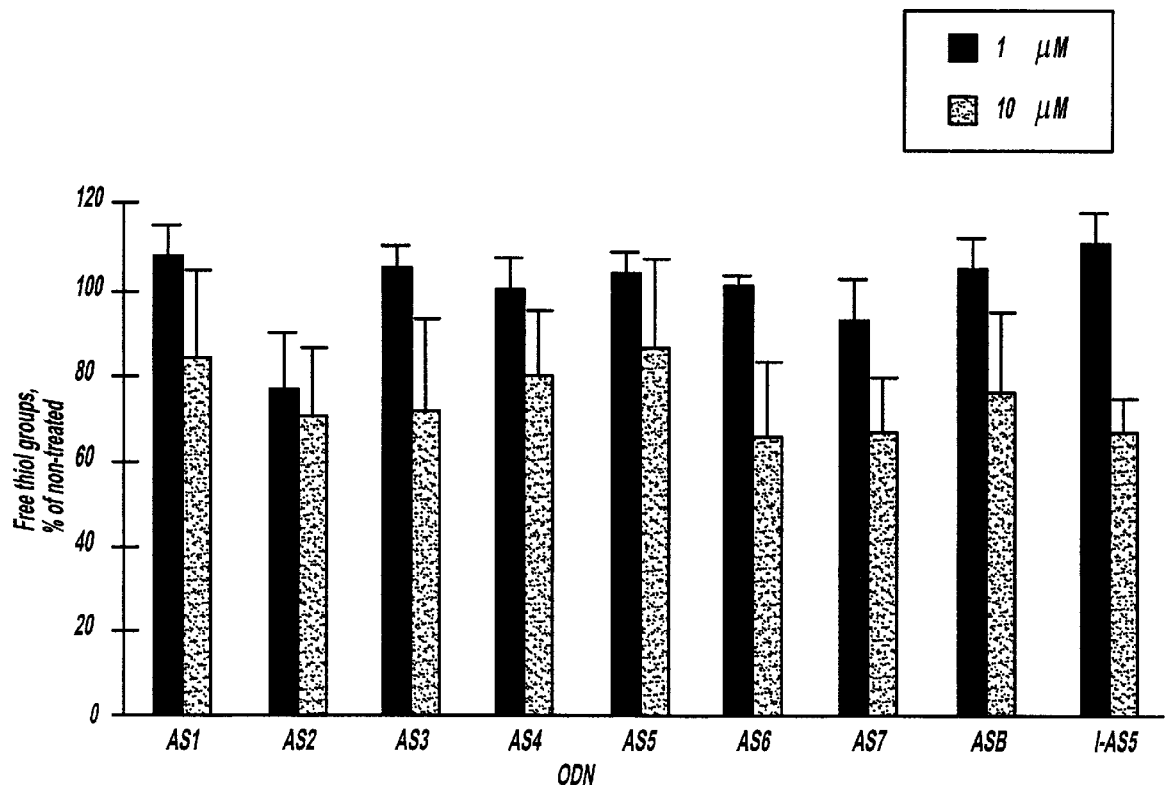

To evaluate neurotoxicity, the number of live cells was determined according to the content of free thiol groups in in situ lysed cells. The rate of acetylthiocholine hydrolysis was the measure of AChE activity. The effects of each ODN on cell survival were studied by quantitating the reactive free thiol groups in Triton X-100-lysed cells as a measure of cell number. This measurement was fast, convenient and simple to perform; a linear relationship was found between the number of cells plated in individual wells and the content of free thiol groups in the culture (FIG. 6A). A similar relationship was observed for NGF-treated cells. A reduction of >20% in free thiol groups was taken as an indication of toxicity. At a concentration of 1 μM, none of the ODNs reduced the content of free thiol groups in the cultures by more than 5%, except for mAS2. Some toxicity was, however, observed at a concentration of 10 μM, where 5 out of the 9 ODNs (Nos. 1, 3, 5, 6 and 7) reduced the content of free thiol groups by 20–40% (FIG. 6B).

To facilitate the uptake of the ODNs into PC 12 cells, we tested reactive liposomes (Lipofectamine™). Under these experimental conditions, Lipofectamine™ seemed to be extremely toxic to the cells, especially after differentiation, and reduced their number to as low as 10% within 24 hours. Therefore, its use was discontinued.

The capacity of these ODNs to suppress AChE activity was tested separately in three sets of growth conditions; (1) for cells in the absence of NGF, (2) for co-administration of AS-ODNs and NGF, and (3) following 24 hour differentiation with NGF, Table III presents the efficacy of each of the tested ODNs in suppression of AChE activity in various PC12 cultures.

AChE activities in control ODN-treated non-differentiated cells were lower than those in non-treated cells by 9 and 10%. One out of the 7 AS-ODNs, mAS3, suppressed AChE activity in non-differentiated PC12 cells by over 20% (P≦0.01, Student's t-test) (Table III, column A). As expected, an increase of approximately 13% in AChE specific activity was observed 24 hours after addition of NGF, so that acetylthiocholine hydrolysis levels increased from 7.8 to 9.0 nmol/min/10$^3$ cells under these conditions. Co-administration of AS-ODNs with NGF resulted in variable yet apparently effective (12–28%) suppression; however, 16% inhibition was observed also in cells treated with the control ODNs. This, and the large variability between inhibition values in different cultures, indicated that much of the effect of AS-ODNs was primarily sequence-independent under these conditions.

Only one AS-ODN, mAS5, exerted significant (28%, $p \leq 0.01$), more than two-fold control inhibition under co-treatment conditions (Table III, column B). Twenty-four hours later, AChE activity increased further to 11.7 nmol/min/$10^3$ cells. Assuming $10^6$ cells per mg wet weight and 10% protein, this is equivalent to 1.2 μmol/min/mg protein, which is considerably higher than the specific activity of 0.22 μmol/min/mg protein for homogenates of mouse brain cortex found by Berri et al. [1995]. Interestingly, a significant part of this increase was prevented when AS-ODNs were added to cells that had been pre-treated with NGF for 24 hours. In these cells, yet two other AS-ODNs, mAS1 and mAS4, suppressed AChE activities by over 25% and 36%, respectively, as compared with a limited suppression (up to 11%) by control ODNs ($p \leq 0.01$).

mAS3, effective in non-differentiated PC12 cells, and mAS5, effective under co-administration of NGF and AS-ODN, inhibited 21 and 20% of AChE activity in NGF pre-treated cells, respectively (Table III, column C). Of these, mAS3 was more significantly effective than mAS5 ($p \leq 0.01$ vs. $\leq 0.05$).

Figure 7:
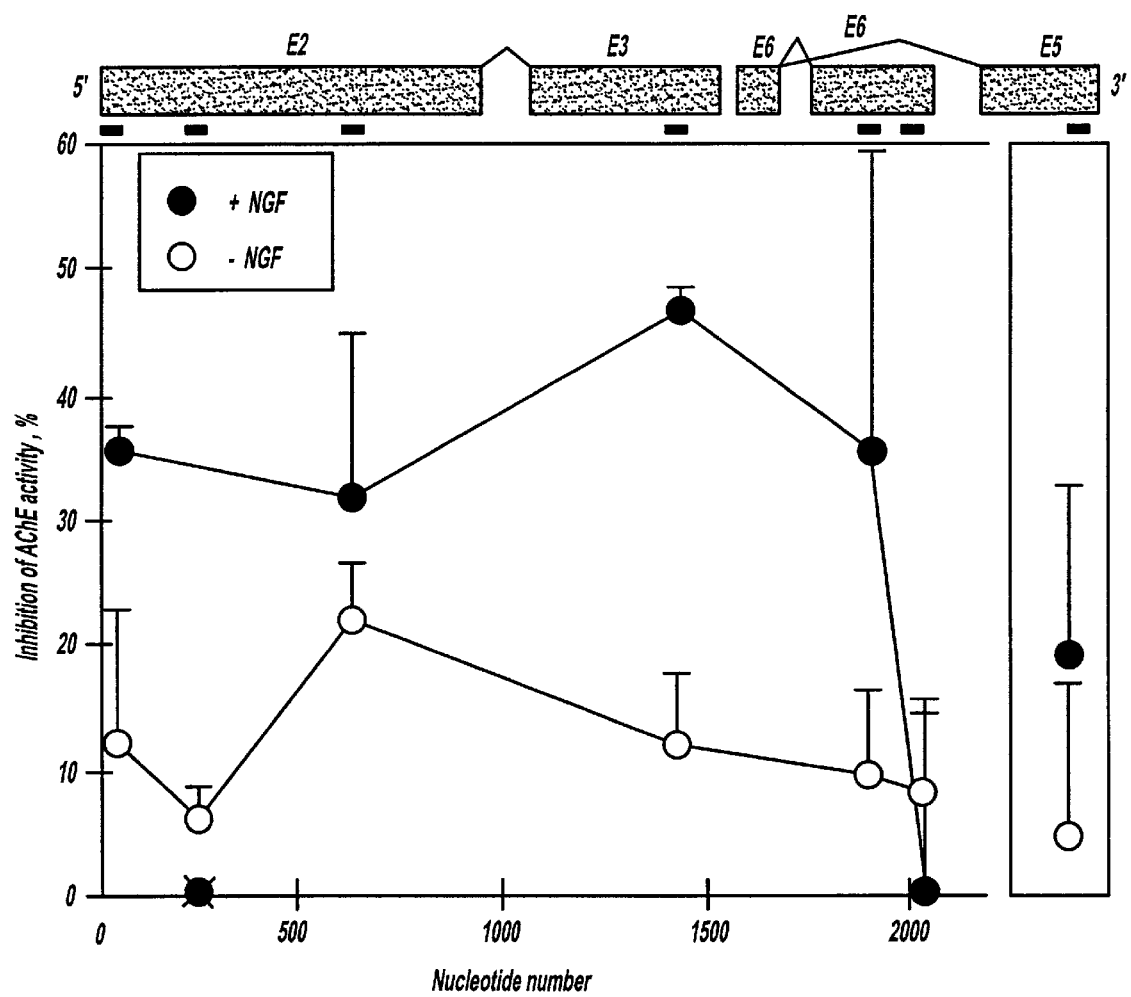
FIG. 7 is a graph showing the efficacy of AS-ODNs at 1 μM depends on NGF induction but not on their target position along the coding region in the ACHEmRNA sequence. Shown are percent inhibition of AChE activity in untreated cultures. Values of AChE in NGF-treated cultures are in filled circles and those for non-differentiated PC12 cells are in empty circles. The data points for each AS-ODN are located below their positions in the ACHEcDNA sequence presented schematically above the graph. Error bars show the standard errors of the mean for 3 wells in each test. The values corresponding to AS5 are located in a separate box to the right, under the alternative E5 exon. Note that for most of the AS-ODNs, inhibition efficacies are higher in the NGF-treated than in non-treated cultures.

FIG. 7 presents the efficacy of each of the AS-ODNs as a function of the position of its target sequence along the ACHEmRNA chain. No pattern relating the sequence position to which an AS-ODN was targeted was detected within the ACHEmRNA chain and its efficacy in suppressing AChE activity, either in non-differentiated or in NGF-pretreated cells. Inactive ODNs included the apparently toxic mAS2 ODN, which did not suppress AChE activity at all, and the 3'-terminal AS-ODN targeted to E6 (mAS-7), which was relatively inefficient under all three growth conditions. Interestingly, mAS5, which was effective in co-treated cells (Table III, column B) and in primary cultured differentiating mouse neurons [Grifman et al., 1997], was relatively inefficacious in non-differentiated PC12 cells. mAS4, which suppressed AChE activity by 36% in NGF pre-treated cells, was rather ineffective both in non-differentiated cells and under co-administration conditions.

To test the possibility that the inhibition of AChE activity in AS-ODN treated cells was due to aptamer effects of the tested oligos on the catalytic activity of the enzyme, the purified recombinant human AChE was incubated for 24 hours in phosphate buffered saline (PBS) including 1% bovine serum albumin and 1 μM of the relevant AS-ODNs. Subsequent measurement of catalytic activates as compared to those of AChE preparations incubated in PBS alone demonstrated that mAS1, mAS3, mAS4, mAS5, and mAS6 did not modify the catalytic activity by more than 3%.

Figure 8A:
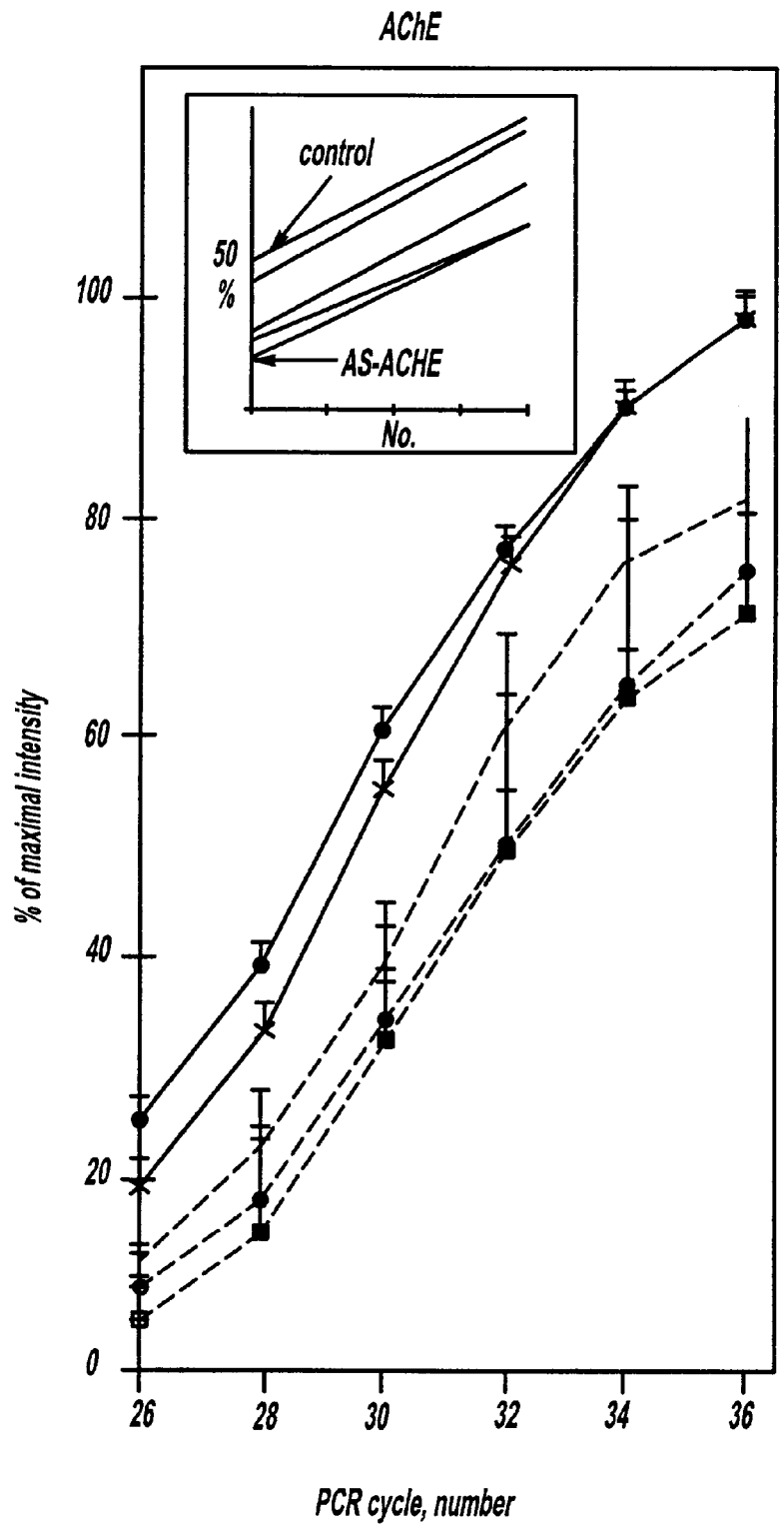
FIGS. 8A–B are graphs of the semi-quantitative measurement of AChE mRNA by kinetic follow-up of RT-PCR. RT-PCR analyses were performed for mRNAs for AChE (A) and actin (B). Amplification products of total RNA extracted from untreated differentiated PC12 cells (none) or cells treated with ODNs (AS1, AS3, AS4, AS6 or AS-B) were subjected to gel electrophoresis and CCD quantification. Shown are percent of maximal fluorescence intensities of 12 μl of ethidium bromide-stained products collected at cycles 18, 20, 22, 24, 26, 28 (for actin mRNA) and 26, 28, 30, 32, 34, 36 (for AChE mRNA). Inset: linear regression analyses of accumulation kinetics were performed only for those time points when product accumulation proceeded at constant pace (cycles 28, 30 and 32 for AChE mRNA, cycles 20, 22, 24 for actin mRNA). Note the shift to the right in the curves derived for AS-ODN treated cells as compared with control cells, and the absence of such shift in the actin mRNA curves.
Figure 8B:
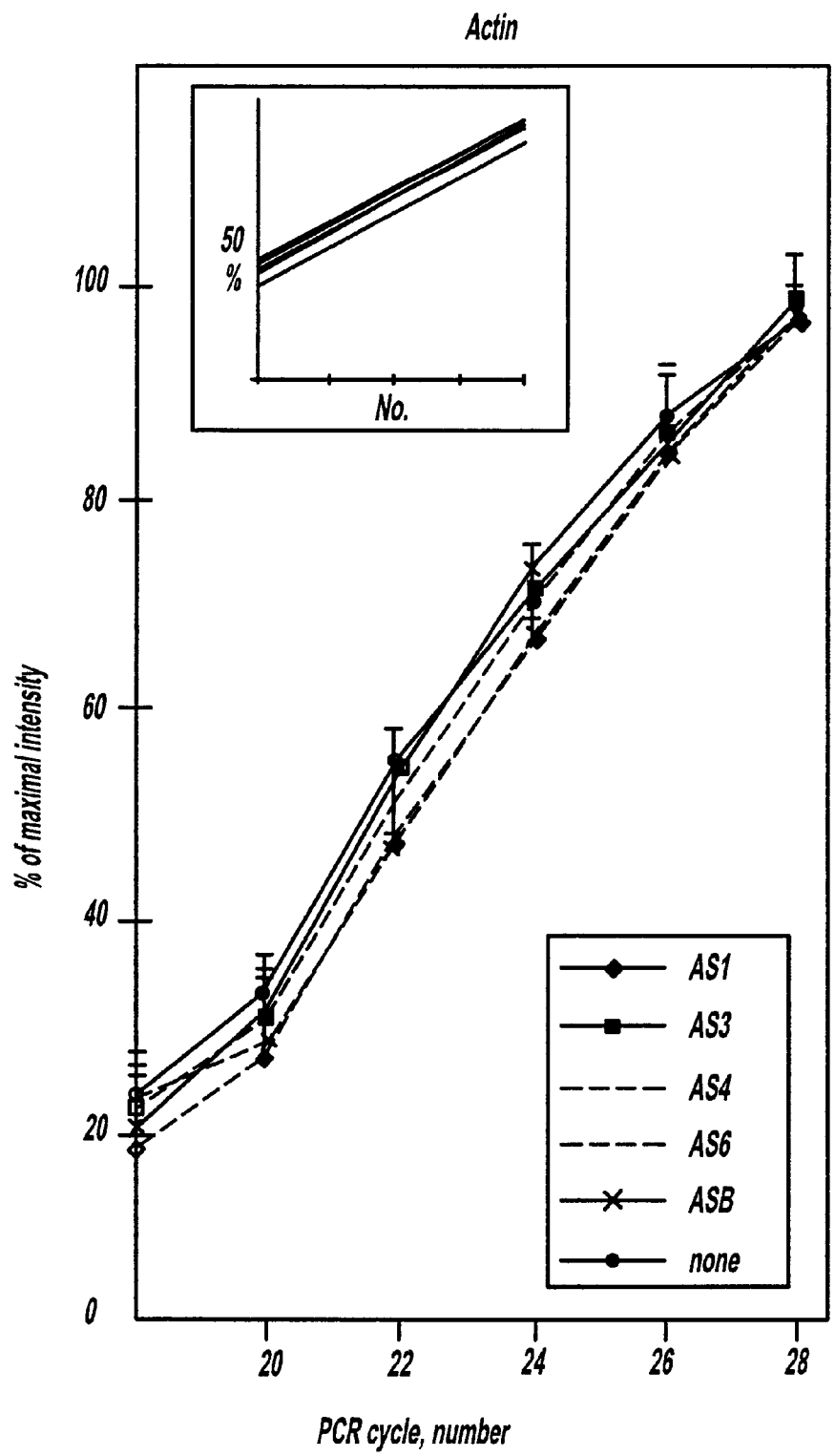

To obtain an independent measure of the inhibition of AChE expression, total RNA was extracted from PC12 cells which were pre-incubated for 24 hours with NGF and then for 24 hours with either mAS1, mAS3, mAS4, mAS6, a control ODN (AS-B) or no ODN. The levels of AChE mRNA in these cells were evaluated by a kinetic follow-up of reverse transcription coupled to PCR amplification (FIG. 8). This semi-quantitative analysis clearly revealed similar kinetics (parallel lines in the accumulation plots) as well as a decrease in AChE mRNA levels in AS-ODNs-treated cells but not in control cells or in those treated with the control ODN (reflected by a shift to the right in the accumulation curve). Moreover, actin mRNA levels, when subjected to the same analysis, remained unchanged in all of these cell cultures, demonstrating the selectivity of ACHEmRNA reduction under the effective AS-ACHE ODNs.

In summary, two out of seven AS-ODNs designed to hybridize with rat ACHEmRNA (mAS1 and mAS4) suppressed AChE activity in PC12 cells that were pre-treated with NGF by over 25%, while leaving cell numbers unaffected. Neither of these was effective in non-differentiated PC12 cells or in NGF co-treated cells, where they did not suppress AChE activity significantly more than the control ODNs. These two ODNs target exons that are common to all the alternatively-spliced forms of ACHEmRNA, a positioning factor which may be relevant to their high efficacies. In contrast, the limited secondary structure predicted by theoretical considerations for mAS3 and mAS4 ($\Delta G:=-4.7$ and $-2.6$ Kcal/mol, respectively) or their low G,C content (40%), seem to be of no significance to their antisense efficacy, as other AS-ODN agents with similar properties (e.g. AS7) were considerably less effective. The FOLDRNA program (University of Wisconsin GCG software package) reveals that mAS4 targets a region with a relatively loose predicted stem-loop composition (not shown). However, mAS1, also effective in NGF pre-treated cells, targets a tightly folded stem region. In addition, it is not apparent that the structure drawn for this 2.3 Kb and mRNA is biologically significant. Thus, none of the standard physical parameters used to characterize AS-ODNs explains the apparent superiority of mAS1 and mAS4 compared to the other AS-ODNs.

An intriguing implication of the Example is that neurons might be considerably more susceptible to AS-ODN inhibition than their undifferentiated precursors. This property may reflect relatively efficient uptake of ODNs, enhanced activity of neuronal RNaseH, more developed vulnerability to bona fide AS mechanism(s), or a combination of all three. The first two possibilities are less likely, since the control ODN was similarly inactive in PC12 cells that had or had not been pre-treated with NGF. This suggested no difference in ODN uptake or in non-specific RNaseH activity. The third option, in turn, indicates distinct mechanisms for specific AS-ODNs functioning in neurons at various stages of differentiation. This option is strengthened by the finding that mAS4 was the most effective in NGF-treated PC12 cells whereas mAS3 was the most effective in undifferentiated PC12 cells. The likelihood of an AS mechanism(s) is further supported by the effective AS-ODN suppression in NGF-stimulated PC12 cells, in spite of the fact that AChE levels increased significantly in such cells. This may be due to enhanced translation, which may increase the susceptibility of AChE mRNA to AS-ODN-mediated destruction. Increased stability of ACHEmRNA in differentiated neurons, as compared with their progenitors, should also be considered, as this was shown in the P19 embryonal neuron cell line [Coleman and Taylor, 1996] and corroborated. However, ACHEmRNA may in differentiated neurons be less protected by cellular protein(s) against RNAse H attack as compared with the less active ACHEmRNA in non-differentiated neurons. Finally, the apparent inhibition of AChE accumulation in NGF pre-treated neurons may reflect a faster turnover of the active enzyme in these cells. Therefore, AS-ODN may be more efficient in NGF-treated neurons due to antisense mechanism(s) supported by potentially enhanced AChE production and faster turnover in these cells, and in spite of the slower turnover of ACHEmRNA in differentiated neurons.

mAS7, targeted to the 3'-region of exon 6, was significantly less effective than those designed against the sequence common to all alternatively-spliced ACHEmRNA transcripts. This was the case in the absence of NGF, under co-treatment conditions and following 24 hour treatment with this differentiation inducing agent. This is not a general rule; on the contrary, AS-ODNs against 3'-regions in other mRNAs were shown to effectively induce destruction of the entire mRNA sequence [e.g. Bennet et al., 1994]. Indeed, a methodical study by Falkler et al. [1994] demonstrated efficacy of ODNs, unrelated to the location of their target sequence in the mRNA. However, mammalian ACHEmRNA is especially rich in G,C base pairs (67% in human ACHE, Soreq et al., 1990). Therefore, it is likely to be tightly folded. Since a truncated human ACHEmRNA bearing only exons 2, 3 and 4 was found to be translatable in Xenopus embryos [Seidman et al., 1997], it is possible that E6-ACHEmRNA is so tightly folded that RnaseH action on its 3'-exon does not lead to destruction of exons 2, 3 and 4, leaving an mRNA which encodes a catalytically active, C-terminally truncated protein.

These findings demonstrate a specificity of several of the AS-ODNs, both for differentiated neurons as target cells and for ACHE expression, showing that specific AS-ODNs can be used to suppress AChE levels in the treatment of diseases associated with cholinergic malfunction or diseases requiring control of cholinergic expression.

Example 5

Testing of AS-ODNs in Transgenic Mice

AS-ACHE-ODNs have been produced and injected which are targeted against both human and mouse AChEmRNA (see Tables I and II). AS-ODNs were protected by one of two modifications: a) phosphorothioate modification of the last three nucleotides (3' phosphorothioated) or b) 3' addition of a 9 base palindromic sequence (SEQ ID No:3) designed to create a nuclease resistant loop (3' looped). The scientific basis for these modifications is presented by Ehrlich et al. [1994].

Materials and Methods
  Enzyme Activity Assays
    Cerebral hemispheres were dissected into cortical and subcortical regions, frozen in liquid nitrogen and stored at −70° C. until used. For AChE activity measurements, extracts were prepared in 10 vol. (wt/vol) 10 mM phosphate buffer containing 1% Triton-X 100 using a glass-glass homogenizer, incubated on ice for 1 hour and microfuged in the cold for 30 minutes. Cleared homogenates were diluted 1:10 and 10 $\mu$l assayed in 200 $\mu$l final volume 0.1 M phosphate buffer (pH 7.4), 0.5 mM dithiobis-nitrobenzoic acid, 0.1 mM acetylthiocholine. Protein determinations were performed using a commercial assay kit (Promega). Enzyme-antigen immunoassay was performed using a species-specific monoclonal antibody (mAb 101-1) to identify AChE of human origin in homogenates.
  RNA Extraction
    Isolation of RNA was made by the RNA-Clean™ method (Angewandte Gentechnologic Systeme GmbH, Heidelberg, Germany). Samples were homogenized in 0.8 ml RNA-Clean and transferred to Eppendorf tubes. 80 $\mu$l chloroform was added to the homogenates and stored for 5 minutes at 4° C. Samples were then centrifuged for 15 minutes and the aqueous phase was collected into new Eppendorf tubes. 0.4 ml of isopropanol was added for 45 minutes at 40° C. RNA precipitates were later centrifuged for 15 minutes and washed once with 0.8 ml of 70% ethanol.
  RT-PCR Amplification
    RT-PCR was performed essentially as described [Beeri et al., 1995] using specific primers for human AChE and mouse AChE, CHAT, actin, and synaptophysin. Cycling reactions were performed at 69° C. RT-PCR was performed in a thermal cycler (GeneAmp PCR System 9600, Perkin-Elmer Cetus Corp. South San Francisco, Calif.). Each tube contained a final volume of 10 $\mu$l, consisting of 2 $\mu$l RNA sample, 3 $\mu$l DDW, 1 $\mu$l dNTPs (4 mM), 0.5 $\mu$l hexamers (2.5 $\mu$M), 2 $\mu$l 5 X PCR buffer, 0.25 $\mu$l HPRI, 1 $\mu$l DDT (100 mM) and 0.25 $\mu$l RT enzyme. After 40 minutes at 37 ° C., 40 $\mu$l of PCR reagents were added, so that total volume in the tubes was 50 $\mu$l. PCR reagents consisted of 4 $\mu$l 10 X PCR buffer 30.75 $\mu$l DDW, 2.5 $\mu$l primer (+, 10 $\mu$M), 2.5 $\mu$l primer (−, 10$\mu$M) and 0.25 $\mu$l of Taq DNA polymerase. Resultant PCR products were electrophoresed on 1.5% agarose gels and visualized under UV illumination following staining with ethidium bromide.

In Vivo Injections
    Protocols for delivering antisense oligonucleotides to transgenic mice in vivo by intravenous (i.v.; tail vein), intraperitoneal (i.p), and intracerebroventricular (i.c.v) routes were developed. To test the validity of these various administration routes, 12–15 day-old mice were used that can be later used to test early prevention schemes.
  i.v.
    12-week-old ACHE transgenic mice were placed briefly under a warming lamp, injected into the tail vein with 5 $\mu$g/gr body wt. oligonucleotide in a volume of 0.1 ml in PBS, and sacrificed 18 hours later by decapitation.
  i.p.
    Mice were injected intraperitoneally with 5 $\mu$g/gr body wt oligonucleotide (0.5 mg/ml). Both single injection and multiple injection protocols were explored. For multiple injections, animals were injected at 24 hour intervals for 3 days. Mice were sacrificed 18 hours following last injection.
  i.c.v.
    10–12 day old ACHE transgenic mice were injected i.c.v. into the left lateral ventricle with 0.2–0.4 $\mu$l oligonucleotide (50–200 $\mu$M) in PBS containing Evans blue as a marker for monitoring accuracy of the injections. For surgery, animals were anesthetized with ether and a small incision was made in the scalp. A small hole was made with a 25 gauge hypodermic needle and injections were performed using a 10 $\mu$l Hamilton syringe. Mice were returned to the mother following a 1–2 hour recovery period and sacrificed 18–40 hours post-injection by decapitation. Brains were excised and cerebellum discarded.
  Results
    Six experiments involving in vivo injections into live animals as described in Table II were performed.
    RNA (200 ng) from cortex of mice injected i.v. with buffer or with AS oligodeoxynucleotides targeted against hACHE (AS1120, SEQ ID No:1; AS1500, SEQ ID No:2) or mACHE (ASmE2, SEQ ID No:8) were subjected to semi quantitative kinetic follow-up of RT-PCR amplification products as described in herein above. Specific primers were employed to detect hACHE, mACHE or synaptophysin (Syn) mRNAs. cDNA product was collected every third cycle between cycles 21–36, subjected to gel electrophoresis and stained with ethidium bromide. The products from cycles 21–36 are presented in FIG. 2 from left to right. First appearance of cDNA product and/or intensity of bands were taken as measures of original mRNA concentration. For hACHE note the lower intensity of the first two bands (cycles 27,30) in all antisense oligodeoxynucleotide treated mice compared to buffer injected control. For mACHE note that the first appearance of product in the ASmE2 treated mouse is delayed by three cycles compared to both buffer injected and hAS injected mice. The control synaptophysin mRNA levels were identical in all samples indicating that an approximately equal amount of RNA was introduced into each PCR reaction and that AS-ODNs did not cause non-sequence dependent cellular toxicity.

Levels of AChE activity in cortex of mice injected with buffer or with AS oligodeoxynucleotides are presented in nmol substrate hydrolyzed/min/ug protein in chart in FIG. 2. There is a decline in AChE activity in the cortex of the two mice injected with AS1500. As shown in FIG. 3, antisense oligonucleotides injected i.c.v. give a reduction in AChE catalytic activity in subcortical regions.

No acute toxic effects were observed in any AS-ODN treated human transgenic mouse and behavior appeared normal in all treated animals. In vivo experiments were performed on littermates only. AS-ODN targeted against hAChEmRNA resulted in diminished levels of both hAChE- and and mAChE mRNAs (FIG. 2) and dramatically reduced protein levels in one of two animals. AS-ODN against mAChEmRNA resulted in a 3 cycle delay in appearance of RT-PCR product in one animal (approx 8-fold reduction in mRNA). When 100 pmole (approx 1 ug) AS-ODN against hAChE- or mAChE- mRNA was delivered i.c.v. to 15 day old mice, 2 of 3 mice in each group displayed total AChE activities >1 S.D. below the mean activity measured in buffer injected animals 40 hours post injection (FIG. 3).

The above results in combination with Examples 7 and 8 herein below demonstrate that the human transgenic mouse model provides a model for testing human AS-ACHE-ODNs for efficacy.

Example 6

Cortico-Hippocampal Brain Slices are Useful as an Ex Vivo System for Evaluating Anti-ACHE-ODNs Efficiency in Mammalian Brain For the first stage in the development of antisense (AS) oligodeoxynucleotide (ODN) therapies directed against the human ACHE gene in brain, it is essential to have a rapid and convenient model for screening candidate ODNs in a heterogeneous population of cells of the mammalian central nervous system (CNS). To this end, applicants established an assay system utilizing cortico-hippocampal brain slices from mice, including transgenic mice carrying the human ACHE gene, together with electrophysiological, biochemical, and molecular analyses.

In this assay 400 $\mu$M murine brain slices can be maintained in vitro for at least 11 hours after which intact, PCR-amplifiable RNA and catalytically active AChE protein may be prepared. Moreover, brain slices are amenable to cytohistochemical analyses including in situ hybridization, cytochemical activity and immunohistochemical staining to determine the precise localization of AChE mRNA and protein expression in various brain regions. Using this system, applicants have demonstrated that application of various acetylcholinesterase (AChE) inhibitors including tacrine (THA, tetrahydroamino-acridine, Cognex®)—the first FDA-approved Alzheimer's disease (AD) drug—induce a 2-fold increase in AChE activity that is preceded by enhanced levels of a specific AChE-encoding messenger RNA. This elevation in AChE activity was associated with enhanced neuronal excitability and is accompanied by changes in the expression of additional genes important in neuronal activity.

Thus, in comparison to cell culture systems, the cortico-hippocampal brain slice system offers a convenient in vitro model to examine the efficacy and mode of action of antisense oligonucleotides targeted against AChEmRNA on primary CNS neurons in the context of their natural surrounding tissues while maintaining many native cholinergic signaling pathways at least partially intact. The main advantage of this approach over in vivo studies is that it overcomes the technical limitations imposed by the blood-brain-barrier by facilitating direct access to brain tissue for the administration of drugs. Moreover, it allows for multiple experimental analyses to be performed on tissues extracted from a single mouse, dramatically reducing the number of animals sacrificed for this research.

Method

For preparation of brain slices, mice were anesthetized with nembutal (60 mg/kg) and decapitated. Brains were removed into ice cold NSR buffer (124 mM NaCl, 3 mM KCl, 2 mM $MgSO_4$, 1.25 mM $NaH_2PO_4$, 26 mM $NaHCO_3$, 10 mM D-glucose, 2 mM $CaCl_2$; pH 7.4) Continuously aerated with 95% $O_2$/5% $CO_2$. Vibrotome sections (400 $\mu$m) were prepared and maintained in aerated NSR buffer at room temperature. Slices were allowed to rest undisturbed at least 1 hour before any additional manipulations were performed. Slices were transferred to individually aerated bottles allowing at least 2.5 ml buffer per 2 slices and the concentration of KCl raised to 8 mM to hyperpolarize the cells prior to the addition of inhibitors.

Results

Transcriptionally regulated shutoff of cholinergic neurotransmission following cholinergic hyperactivation: During acute stress reaction central cholinergic pathways are fully activated. To explore the molecular consequences of cholinergic hyperactivation, we subjected normal FVB/N mice to a forced swimming stress protocol or exposed cortico-hippocampel brain slices to cholinesterase inhibitors and searched for accompanying changes in brain gene expression. Both stress in vivo and AChE inhibition in vitro stimulated rapid and specific increases in "readthrough" AChEmRNA encoding a soluble hydrophilic AChE with potentially greater intercellular accessibility than the classic synaptic form of the enzyme.

In situ hybridization revealed "readthrough" AChEmRNA transcripts in cell bodies and apical processes of pyramidal neurons within cortical layers 2, 3, 4 and 5 in brain sections from mice injected with the anti-AChE pyridostigmine, as compared with weaker, more restricted labeling in cell bodies located in layer 2 and layer 5 neurons from controls. Increased AChEmRNA levels induced up to 3-fold enhanced levels of catalytically active enzyme in hippocampus and cortex but not in cerebellum within 5 hours. Stress-enhanced AChE activity was characterized by increased heterogeneity and overall faster migration in non-denaturing gel electrophoresis. In contrast, both stress and inhibition of AChE stimulated pronounced reductions in ChATmRNA levels, suggesting that a bimodal mechanism comprised of suppressed acetylcholine synthesis and enhanced acetylcholine hydrolysis works to shut down cholinergic neurotransmission following acute hyperactivation. Although both treatments resulted in increased c-fos mRNA levels indicating neuronal excitability, no changes were observed in synaptophysin mRNA levels, demonstrating the selectivity of this "cholinergic" feedback response. In brain slices treated with AChE inhibitors increased neuronal excitability, paired-pulse facilitation, and mRNA changes were blocked by both BAPTA-AM and tetrodotoxin, indicating that these processes are mediated by increases in intracellular Ca++ and/or Na+ influx.

These experiments demonstrate the utility of the brain slice system in monitoring changes in ACHE gene expression and the utility of ACHE transgenic mice as a novel model for studying the efficacy of AS-ACHE-ODNs.

Tacrine-Induced Elevation of AChE Expression

Tacrine is a potent reversible AChE inhibitor which relieves cognitive symptoms in 30–50% of mildly to moderately affected AD patients. The observation that irreversible inhibitors such as DFP or pyridostigmine induce lasting changes in the expression of genes relating to cholinergic pathways, including feedback pathways elevating AChE levels, suggested that tacrine may induce similar responses. To examine this possibility, tacrine was applied at a concentration of 5 ×10$^{-7}$ M to brain slices for 75–90 minutes and examined AChE activity in detergent extracts. Under these conditions, AChE activities of 26–186% above those measured in control untreated slices were observed.

These observations reinforce the utility of cortico-hippocampal brain slices in the study of AChE gene expression and provide for the use of tacrine in studies of the efficacy of antisense oligonucleotides targeted against AChEmRNA in suppressing AChE biosynthesis in a sensitive, short time-frame model. Moreover, they emphasize the importance of finding alternatives to the current cholinesterase inhibitor approach to treating AD.

Example 7

Deficient Performance of HaCHE Transgenic Mice in Memory Tests Based on Social Exploration or Taste Social Exploration Applicants previously demonstrated impaired performance of transgenic FVB/N mice expressing human acetylcholinesterase (AChE) in cholinergic brain neurons in the Morris water maze for spatial learning and memory [Beeri et al., 1995]. Although one-month-old transgenic mice perform similarly to control mice, progressive deterioration in the performance of transgenic mice is observed to the age of 6–8 months at which point they have difficulty performing the task altogether. Together with neuropathological analyses [Beeri et al., submitted], these findings appear to depict a chronic cholinergic imbalance leading to late-onset, progressive cognitive deficiencies—a novel model for the cholinergic impairments associated with Alzheimer's disease. However, recent studies revealed severe visual impairments in AChE transgenic mice from around two weeks of age. Since performance in the Morris water maze purportedly depends primarily on visual clues, it became important to conduct additional studies using a learning/memory paradigm that does not require intact visual networks to validate the model.

The experimental approach: To study the progressive cognitive deficits observed in AChE transgenic mice by an approach independent of visual functioning, the behavior of these mice in a test of social exploration was observed. The test includes exposure of an adult mouse, either transgenic or control, to an unknown juvenile. This initiates an olfactory response of sniffing which lasts approximately 240 seconds. When the young mouse is removed and then immediately presented again (second presentation), the sniffing period shortens to about 80 seconds. This is a test of working memory and takes place similarly in transgenics and controls. When a different young mouse is substituted for the second presentation, it will be sniffed ca. 200 seconds, indicating a clear distinction between exploration of "same" and "different".

Ten minutes later, an adult control mouse will need 150 seconds to ascertain recognition. After 20 minutes it will need 200 seconds and after 30 minutes it will repeat the whole ritual as if this same mouse was not known to it at all. In the case of the transgenic mice "same" is treated as "different" even after a lapse as brief as 10 minutes, demonstrating a clear deficiency in this behavior (FIG. 9A).

Effect of Tacrine

This short-term behavior is described in the literature as dependent on cholinergic pathways, and emphasizes that cholinesterase inhibitors extend the explorative memory. Tacrine as shown in Example 6 induced elevation of AChE expression and utilizing this test, the effect of tacrine on hAChE transgenic mice was tested. As shown in FIG. 9B i.p. injection of 1 mg/ml tacrine extended short-term memory to 20 minutes in young (6 week old) transgenic mice.

This Example provides additional data that hAChE-transgenic mice indeed suffer from progressive cognitive deficits that can be traced to cholinergic malfunction(s) that respond, at least in part, to anticholinesterase therapy for some time. Further the social exploration test offers a relatively simple, rapid test to examine the efficacy of anticholinesterase therapies, including antisense oligonucleotides targeted against human AChE mRNA.

Taste Aversion Memory

Figure 10:
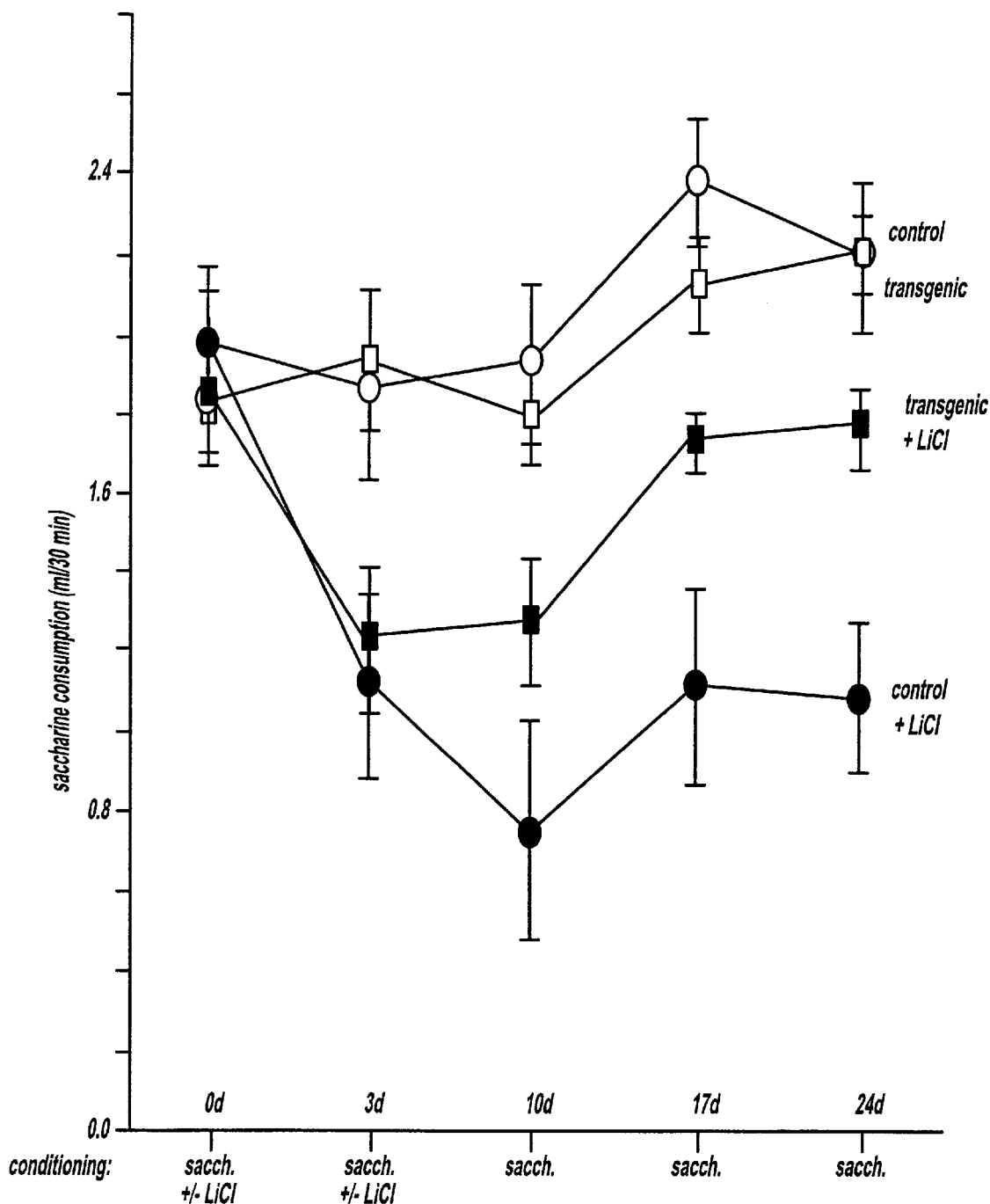
FIG. 10 is a bar graph of deficient performance of AChE transgenic mice in a taste aversion test demonstrating that hAChE transgenic mice learn but do not have long-term memory.

Unlike the social exploration test, the taste aversion is designed to distinguish between defects in learning and long-term memory. Groups of non-transgenic and transgenic mice (10 mice per group), controls were saline-injected, were established. The mice were kept thirsty for 20 hours and then allowed to drink saccharine-sweetened water. The mice drank a volume of 2 ml (about 10% of their body weight). Thirty minutes later they are injected with a nausea-causing lithium chloride solution. After 3 days, they were tested for learning and short-term memory with a saccharine challenge. In general, the mice drank only 1.2 ml, that is they learned and remembered that the sweet taste causes nausea. The mice then received a second conditioning with the lithium chloride. Up to this point both the control and transgenic mice responded the same (FIG. 10).

To test long term memory, once a week, for several weeks after the initial challenge and conditioning, the mice were given saccharine water (but no lithium). Control mice continued to drink less for weeks showing long term memory. However, the transgenics gradually forgot, returning to full volume drinking within less than a month (FIG. 10).

The reference memory function required to stabilize the taste aversion experience depends on cholinergic function which is impaired in the transgenic mice.

Example 8

Effect of AS-ODN on Transgenic Mice in the Social Exploration Test

An evaluation of 2-O-methyl AS-ODNs targeted to AChEmRNA to promote improved performance of ACHE transgenic mice in the learning and memory test of Social Exploration and to correlate changes in behavior with modulations in AChE protein and/or RNA levels. The experiment was repeated twice with the same results. Following is the results from one representitive experiment.

Methods

Cannulation

Cannula were stereotaxically implanted into a ventricle of 5-month old HpACHE mice approximately 2 weeks prior to the experiment and housed singly during the recovery period.

Oligonucleotides and In Vivo Administration 5 mM 2-O-methyl (last three 3' nucleotides) oligonucleotides targeted against murine AChE (ASmACHE3-Me; mAS3; SEQ ID No:11) or BuChE (ASmBCHE-Me; mASB) were combined with 13 mM of the lipophilic transfection reagent DOTAP (Boehringer Mannheim) in phosphate buffered saline and incubated for 15 minutes at 37° C. prior to first injection. 1 $\mu$l(25 ng) ODN was infused icv over a period of 1–2 minutes, 2 times, at 24 hour intervals. Mice were subjected to the social exploration test and sacrificed 24 hours following the last administration of ODN.

Sequences mAS3: 5'-CTGCAATATTTTCTTGCACC-3' (20 mer; SEQ ID No:11)

mASB: 5'-GACTTTGCTATGCAT-3' (15 mer; SEQ ID No:15)

Social Exploration Test

Mice were placed in a cage with a glass front panel together with an unknown juvenile mouse for 4 minutes and the times invested by the adult mouse in exploratory contact with the juvenile recorded by an observer. At the end of the "baseline" test, the juvenile was removed from the cage. Ten minutes later, the same juvenile was reintroduced to the cage and the exploratory time recorded ("test"). The ratio of test:base time determined the "performance ratio" (PR). PR<1 represents "learning and memory".

Cannulated mice were evaluated in social exploration 24 hours prior to the first administration of ODN (PR1) and 24 hours following the last administration (PR2). PR2:PR1 was taken as a measure of oligonucleotide-induced improvements in learning and/or memory.

Biochemistry

Animals were sacrificed by cervical dislocation, brains removed; hippocampus and cortex were dissected from each hemisphere, frozen on dry ice, and stored at −70(C until used. Low-salt-detergent extracts were prepared in cold 0.1 M phosphate buffer (pH 7.4) containing 1% Triton X-100 (1:9 wt/vol), and assayed for AChE activity using a colorimetric assayed based on the hydrolysis of acetylthiocholine (1 mM) (see herein above, Ellman et al, 1961). Protein determination was performed using the detergent-compatible (DC) kit from Biorad which is based on the assay of Lowry.

Results

Tables 4 (experimental) and 5 (control) present the results. The AChE-transgenic mice which suffer from progressive cognitive deficits (see Example 7) that can be traced to cholinergic malfunction(s) that respond, at least in part, to anticholinesterase therapy. As can be seen, the AS-ODN of SEQ ID No:3 improved performance in the transgenic mice. An anti AChE-ASODN can promote improved learning following 48 hours administration. ODN-mediated modulations of AChE proteins levels are reversible within 24 hours of administration.

Throughout this application, various publications, including U.S. patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Antisense Oligonucleotides

| NAME | SEQUENCE | SPECIES | PROTECTION | POSITION | MW | SEQ ID |
|---|---|---|---|---|---|---|
| 1. ASmE2 | 5'GGGAGAGGAGGAGGAAGAGG3' | mouse | 3' PS x3 | 51 | 6994 | SEQ ID No:8 |
| 2. invmE2 | 5'GGAGAAGGAGGAGGAGAGGG3' | mouse | 3' PS x3 | 51 | 6994 | SEQ ID No:9 |
| 3. ASmE5 | 5'AGAGGAGGGACAGGGCTAAG3' | mouse | 3' PS x3 | 67 in E5 | 6889 | SEQ ID No:10 |
| 4. S-h-ACHE | 5'ATGAGGCCCCCGCAG3' | human | 3' PS x3 | 140 (Soreq 1990, PNAS) | 5068 | SEQ ID No:11 |
| 5. AS - 1120L | 5'ACGCTTTCTTGAGGCCGCGAAGCG3' | human | loop | 1119 (Soreq 1990, PNAS) | 7969 | SEQ ID No:1 and SEQ ID No:3 |
| 6. AS - 1500L | 5'GGCACCCTGGGCAGCCGCGAAGCG3' | human | loop | 1507(Soreq 1990, PNAS) | 7989 | SEQ ID No:2 and SEQ ID No:3 |
| 7. ASmE2L | 5'GGGAGAGGAGGAGGAAGAGGCGCGAAGCG3' | mouse | loop | 51 | 9914 | SEQ ID No:8 and SEQ ID No:3 |

3' PS xn = last n nucleotides contain phosphorothioate internucleotidic bonds
loop = 9 last nucleotides at the 3' are designed to form a loop, and are not part the original sequence
AS = antisense sequence
S = sense control sequence
inv = inverse (control) sequence

TABLE 2

| Table II series no. | delivery | oligo | no. of mice | dose | duration | analysis |
|---|---|---|---|---|---|---|
| 1 | i.v. | buffer | 2 | — | 20 h. | protein assay |
| | | AS-1120L | 2 | 150 ug | | RT-PCR |
| | | AS-1500L | 2 | 120 ug | | |
| | | ASmE2 PS | 1 | 120 ug | | |
| | | | total = 7 | | | |
| 2 | i.c.v. | buffer | 1 | 50 uM | 18 h. | protein assay |
| | | ASmE2 3'L | 1 | 200 nl | | histology |
| | | AS-1120L | 2 | | | |
| | | | total = 4 | | | |

TABLE 2-continued

| Table II series no. | delivery | oligo | no. of mice | dose | duration | analysis |
|---|---|---|---|---|---|---|
| 3 | i.c.v. | buffer | 2 | 50 uM | 24 h. | protein assay |
| | | ASmE2 PS | 2 | 200 nl | | |
| | | inv. mE2PS | 3 | | | |
| | | ASmE2 3'L | 2 | | | |
| | | uninjected | 1 | | | |
| | | | total = 10 | | | |
| 4 | i.p. | buffer | 2 | 5 ug/gr | 4 d | protein assay |
| | | ASmE2 PS | 2 | body wt | | |
| | | inv. mE2 PS | 2 | | | |
| | | ASmE2 3'L | 2 | | | |
| | | | total = 8 | | | |
| 5 | stress+ i.p. | buffer | 2 | 5 ug/gr | 4 d | protein assay |
| | | ASmE2 PS | 2 | body wt | | |
| | | inv. mE2 | 1 | | | |
| | | | total = 5 | | | |
| 6 | i.c.v. | buffer | 3 | 250 uM | 48 h. | protein assay |
| | | ASmE2 3'L | 3 | 400 nl | | RT-PCR |
| | | AS-1120L | 3 | | | |
| | | | total = 9 | | | |

TABLE III

Inhibition of AChE activity by 1 $\mu$M AS-ODNs in PC12 cells[a]

| | A. 24 h ODN, no NGF | | B. 24 h ODN + NGF | | C. 24 h NGF, then 24 h ODN + NGF | |
|---|---|---|---|---|---|---|
| | sp. act. nmol/min/10³ cells | inhibition of AChE activity, % | sp. act. nmol/min/10³ cells | inhibition of AChE activity, % | sp. act. nmol/min/10³ cells | inhibition of AChE activity, % |
| AS1 | 6.7 ± 0.6 | 15 ± 6 | 7.8 ± 0.8 | 16 ± 7 | 8.5 ± 0.7 | 27 ± 7 |
| AS2 | 7.1 ± 0.4 | 11 ± 4 | 7.9 ± 0.3 | 12 ± 6 | 12.1 ± 0.8 | 4 ± 3 |
| AS3 | 6.1 ± 0.1 | 20 ± 5 | 8.0 ± 0.7 | 17 ± 9 | 9.4 ± 0.7 | 21 ± 8 |
| AS4 | 6.7 ± 0.6 | 16 ± 5 | 8.4 ± 0.2 | 15 ± 10 | 7.5 ± 0.1 | 36 ± 5 |
| AS5 | 7.2 ± 0.1 | 9 ± 5 | 6.5 ± 0.2 | 28 ± 5 | 10.4 ± 0.1 | 11 ± 6 |
| AS6 | 7.0 ± 0.3 | 12 ± 5 | 6.9 ± 0.4 | 23 ± 6 | 9.8 ± 0.7 | 20 ± 10 |
| AS7 | 6.8 ± 0.5 | 13 ± 5 | 7.8 ± 0.1 | 14 ± 9 | 11.4 ± 0.4 | 5 ± 3 |
| AS8 | 7.3 ± 0.1 | 10 ± 5 | 7.8 ± 0.2 | 16 ± 8 | 11.4 ± 1.1 | 11 ± 5 |
| I-AS5 | 7.4 ± 0.1 | 9 ± 5 | 7.9 ± 0.7 | 16 ± 8 | 12.7 ± 1.4 | 0 ± 1 |
| none | 7.8 ± 0.4 | NA | 9.0 ± 0.4 | NA | 11.7 ± 0.3 | NA |

[a]Averages of 6 cultures measurements and standard errors of the mean are presented for rates of hydrolysis of acetylthiocholine by 1,000 cells. NA = non-applicable. Background due to spontaneous hydrolysis of acetylthiocholine (7.3 nmol/min) was subtracted.

TABLE 4

AS3 Treated

| | PRETREATMENT | | | POSTTREATMENT | | | TREATMENT VALUE | |
|---|---|---|---|---|---|---|---|---|
| Animal | Baseline | Test | Performance Ratio (PR1) | Baseline | Test | Performance Ratio (PR2) | PR1/PR2 | AChE Activity hippocampus |
| 2 | 97 | 142 | 1.46 | 93 | 84 | 0.90 | 0.62 | 552.30 |
| 4 | 150 | 147 | 0.98 | 152 | 131 | 0.86 | 0.88 | 125.80 |
| 5 | 100 | 124 | 1.24 | 140 | 89 | 0.64 | 0.51 | 862.00 |
| 6 | 155 | 153 | 0.99 | 179 | 134 | 0.75 | 0.76 | 122.10 |
| 10 | 150 | 192 | 1.28 | 221 | 196 | 0.89 | 0.69 | 57.20 |
| Avg | 130 | 151 | 1.19 | 157 | 126 | 0.81 | 0.69 | 343.88 |
| S.D. | 26.1 | 22.4 | 0.18 | 42.4 | 40.3 | 0.10 | 0.12 | 313.31 |

TABLE 5

| | Control ASB | | | | | | | |
|---|---|---|---|---|---|---|---|---|
| | PRETREATMENT | | | POSTTREATMENT | | | TREATMENT VALUE | |
| Animal | Baseline | Test | Performance Ratio (PR1) | Baseline | Test | Performance Ratio (PR2) | PR1/PR2 | AChE Activity hippocampus |
| 1 | 121 | 133 | 1.10 | 133 | 162 | 1.22 | 1.11 | 93.90 |
| 3 | 188 | 182 | 0.97 | 111 | 122 | 1.10 | 1.14 | 89.00 |
| 9 | 143 | 225 | 1.57 | 42 | 70 | 1.67 | 1.06 | 98.70 |
| Avg | 150 | 180 | 1.21 | 95 | 118 | 1.33 | 1.10 | 93.87 |
| S.D. | 27.8 | 37.6 | 0.26 | 38.9 | 37.7 | 0.24 | 0.03 | 3.96 |

REFERENCES

Agarwal et al., 1991. Proc. Natl. Acad. Sci. USA, 88:7595.

Agrawal, 1996. Antisense oligonucleotides: towards clinical trials, TIBTECH, 14:376.

Akhter et al, 1991, Nuc. Res. 19:5551–5559.

Andres et al., 1997. ACHE transgenic mice display embryonic modulations in spinal cord CHAT and neurexin gene expression followed by late-onset neuromotor deterioration. Proc. Natl. Acad. Sci. USA 94, 8173.

Beeri et al., 1995. Transgenic expression of human acetylcholinesterase induces progressive cognitive deterioration in mice. Current Biology, 5:1063-1071.

Beeri, et al., (1997; Submitted for publication). Enhanced hemicholinium binding and attenuated dendrite branching in cognitively impaired ACHE transgenic mice.

Ben Aziz-Aloya et al., 1993. Expression of a human acetylcholinesterase promoter-reporter construct in developing neuromuscular junctions of Xenopus embryos, Proc. Natl. Acad. Sci. USA, 90:2471–2475.

Bennett et al., 1994. Inhibition of endothelial cell adhesion molecule expression with antisense oligonucleotides. J. Immunol. 152:3530–3540.

Betz et al., 1994, Basic Neurochem. Molecular Cell, (Raven Press Ltd, NY) 5th Ed., 681–699

Boado and Pardridge, 1992. Complete protection of antisense oligonucleotides against serum nuclease degradation by an avidin-biotin system. Bioconjug. Chem. 3, 519–523.

Bickel, et al., 1993. Pharmacologic effects in vivo in brain by vector-mediated peptide drug delivery, Proc. Natl. Acad. Sci. USA 90(7):2618–2622.

Brem et al., 1993. Polymers as controlled drug delivery devised for the treatment of malignant brain tumors, Eur. J. Pharm. Biopharm 39:2–7

Caceres and Kosik, 1990. Nature, 343:461.

Calabretta, et al, 1996. Antisense strategies in the treatment of leukemias, Semin. Oncol. 23:78.

Coleman and Taylor, 1996. Regulation of acetylcholinesterase expression during neuronal differentiation. J. Biol. Chem. 271:4410–4416.

Coyle, et al, 1983. Alzheimer's diseases: A disorder of cortical cholinergic innervation. Science 219:1184–1190.

Crooke, 1995. Progress in antisense therapeutics, Hematol. Pathol. 2:59.

Darboux, et al., 1996. The structure-function relationships in Drosophila neurotactin shows that cholinesterasic domains may have adhesive properties, EMBRO J. 15:4835–4843.

Eckstein 1985. Ann. Rev. Biochem. 54:367–402.

Ehrlich et al., 1994. Use of partially phosphorothioated "Antisense" oligodeoxynucleotides for sequence-dependent modulation of hematopoiesis. Antisense Res. Develop. 4:173–183.

Ellman et al., 1961. A new and rapid calorimetric determination of acetylcholinesterase activity. Biochem. Pharmacol. 7:88–95.

Galileo et al., 1991. J. Cell. Biol., 112:1285.

Gewirtz, 1993. Oligodeoxynucleotide-based therapeutics for human leukemias, Stem Cells Dayt., 11:96.

Greene, and Tischler, 1976. Establishment of a noradrenergic clonal line of rat adrenal phaeochromocytoma cells which respond to nerve growth factor. Proc. Natl. Acad. Sci. USA. 73:2424–2428.

Grifman et al., 1995. Impairment of neurite extension and apoptosis-dependent DNA fragmentation in primary neuronal cell cultures administered with an ACHE antisense oligonucleotide (Abstract) J. Neurochem., 65 (supplement) S82D.

Grifman et al., 1997. Potential antisense oligonucleotide therapies for neurodegenerative diseases. In Concepts in Gene Therapy, M. Strauss and J. A. Barranger, eds. (Walter de Gruyter & Co., Berlin)

Hanania, et al 1995. Recent advances in the application of gene therapy to human disease, Am. J. Med., 99:537.

Iyer et al. 1990. J. Org. Chem., 55:4693–4699.

Jasmin et al. (1993) "Compartmentalization of acetylcholinesterase mRNA and enzyme at the vertebrate neuromuscular junction" Neuron. 11:467–477.

Johansson and Nordberg, 1993. Pharmacokinetic studies of cholinesterase inhibitors. Acta neural. scad. Suppl. 149:22–25.

Jones et al., 1995. The effect of acetylcholinesterase on outgrowth of dopaminergic neurons in organotypic slice culture of rat midbrain, Cell Tissue Res., 279:323–330.

Juliano and Akhtar, 1992. Liposomes as a drug delivery system for antisense oligonucleotides. Antisense Res. Develop 2, 165–176.

Karpel et al. 1994. Expression of three alternative acetylcholinesterase messenger RNAs in human tumor cell lines of different tissue origins, Exptl. Cell. Res. 210:268–277.

Karpel et al, 1996. Overexpression of alternative human acetylcholinesterase forms modulates process extensions in cultured glioma cells, J. Neurochem. 66:114–123.

Knapp et al., 1994. A 30-week randomized controlled trial of high-dose tacrine in patients with Alzheimer's disease. JAMA, 271:985–991.

Lapidot-Lifson, et al., 1989. Co-amplification of human acetylcholinesterase and butyrylcholinesterase genes in blood cells: Correlation with various leukemias and abnormal megalaryocytopoiesis. Proc. Natl. Acad. Sci. USA, 86:4715.

Lapidot-Lifson, et al, 1992. Cloning and antisense oligodeoxynucleotide inhibition of a human homolog of cdc2 required in hematopoiesis, Proc. Natl. Acad. Sci. USA, 89:579.

Layer, 1995. Non-classical roles of cholinesterases in the embryonic brain and possible links to Alzheimer disease, Alzheimer Disease and associated disorders, 9:29.

Lee et al., 1995. Comparative expressed-sequence-tag analysis of differential gene expression profiles in PC-12 cells before and after nerve growth factor treatment. *Proc. Natl., Acad. Sci.* USA 92:8303–8307.

Lefebvre-d'Hellencourt, et al, 1995. Immunomodulation by cytokine antisense oligonucleotides, *Eur. Cytokine Netw.,* 6:7.

Legay et al. 1993a. Cloning and expression of a rat acetylcholinesterase subunit: generation of multiple molecular forms, complementarity with a Torpedo collagenic subunit, *J. Neurochem.* 60:337–346.

Legay et al. 1993b. Expression of a cDNA encoding the glycolipid-anchored form of rat acetylcholinesterase, *FEBS Lett* 315:163–166.

Lev-Lehman et al., 1994. Antisense inhibition of acetylcholinesterase gene expression causes transient hematopoietic alterations in vivo. *Gene Therapy,* 1:127–135.

Lev-Lehman et al., 1997. Antisense Oligomers in vitro and in vivo. In *Antisense Therapeutics,* A. Cohen and S. Smicek, eds (Plenum Press, New York)

Li et al., 1991. Gene structure of mammalian acetylcholinesterase: Alternative exons dictate tissue specific expression, *J. Biol. Chem.* 266:23083–23090.

Li et al., 1993. *J. Biol. Chem.* 268:5790–97.

Loke et al, 1989. *PNAS* USA 86:3474.

Loewenstein-Lichtenstein, et al, 1996. Overlapping drug interaction sites of human butyrylcholinesterase dissected by site-directed mutagenesis. Mol. Pharmacol. 50:1423–1431.

Loewenstein-Lichtenstein, et al, 1995. Genetic predisposition to adverse consequences of anti-cholinesterases in "atypical" BCHE carriers. Nature Medicine 1:1082–1085.

Morrison, R. 1992. *Neuroscience Facts* 3:3.

Morrison, J. 1991. *J. Biol. Chem.,* 266:728.

Owens and Bunge, 1991. *Neuron,* 7:56.

Pardridge, et al., 1992. Blood-brain barrier and new approaches to brain drug delivery. *West J. Med.* 156(3):281–286

Pardridge, 1992. Recent Developments in peptide drug delivery to the brain, *Pharm. Toxicol.* 71(1):3–10

Patinkin, et al, 1990. Manipulations of cholinesterase gene expression modulate murine megakaryocytopoiesis in vitro, *Mol. Cell. Biol.,* 10:6046.

Patinkin, et al., 1994. Antisense inhibition of butyrylcholinesterase gene expression predicts adverse hematopoietic consequences to cholinesterase inhibitors, *Cell. Mol. Neurobiol.,* 14:459.

Rogers, et al, 1996. The efficacy and safety of Donepezil in patients with Alzheimers disease: results of a US multicentre, randomized, double blind, placebo controlled trial. Dementia 7:293–303.

Rosolen et al., 1990. *Cancer Res.,* 50:6316.

Salpeter (1967) "Electron microscope radioautography as a quantitative tool in enzyme cytochemistry I: The distribution of acetylcholinesterase at motor endplates of a vertebrate twitch muscle" *J. Cell. Biol.* 32:379–389.

Scanlon, et al., 1995. Oligonucleotides-mediated modulation of mammalian gene expression, *FASEB J.,* 9:1288.

Seidman, et al., 1995. Synaptic and epidermal accumulations of human acetylcholinesterase is encoded by alternative 3'-terminal exons. *Mol. Cell. Biol.* 15:2993–3002.

Shaw et al., 1991. *Nucleic Acids Res.,* 19:747–750.

Small, et al., 1995. Cholinergic regulation of neurite outgrowth from isolated chick sympathetic neurons in culture, *J. Neurosci.,* 15:144–151.

Soreq, et al., 1990. Molecular cloning and construction of the coding region for human acetylcholinesterase reveals a G+C-rich attenuating structure, *Proc. Natl. Acad. Sci. USA,* 87:9688–9692.

Soreq, et al., 1994. Antisense oligonucleotide inhibition of acetylcholinesterase gene expression induces progenitor cell expansion and suppresses hematopoietic apoptosis ex vivo, *Proc. Natl. Acad. Sci. USA,* 91:7907–7911.

Spitzer and Eckstein 1988. *Nucleic Acids Res.,* 18:11691–11704.

Stein and Cheng, 1993. Antisense oligonucleotides as therapeutic agents—Is the bullet really magical? *Science,* 261:1004.

Sternfield, et al., 1997. Catalytic and non-catalytic acetylcholinesterase functions implied from transgenic ACHE expression in vertebrates. In *Neurotransmitter Release and Uptake,* S. Pogun ed. (Springer-Verlag, Berlin)

Tao-Cheng et al., 1995. Characterization of synaptic vesicles and related neuronal features in nerve growth factor and ras oncogene differentiated PC12 cells. *J. Neurosci. Res.* 42:323–334.

Wagner, 1994. Gene inhibition using antisense oligodeoxynucleotides, *Nature,* 372:333.

Whitesell et al., 1991. *Mol. Cell. Biol.,* 11:1360.

Winker, 1994. Tacrine for Alzheimer's disease; which patient, what dose? JAMA 271: 1023–1024.

Winstein et al., 1991. *J. Cell Biol.,* 112:1205.

Woolf et al., 1990. *Nucleic Acids Res.,* 18:1763–1769.

Yakubov et al, 1989. *PNAS* USA 86:6454.

What is claimed is:

1. A synthetic nuclease resistant antisense oligodeoxynucleotide for selectively modulating human acetylcholinesterase (AChE) production selected from the group consisting of 5'ACGCTTTCTTGAGGC 3' SEQ ID No:1,
5'GGCACCCTGGGCAGC 3' SEQ ID No:2,
5'CCACGTCCTCCTGCACCGTC 3' SEQ ID No:6,
5'ATGAACTCGATCTCGTAGCC 3' SEQ ID No:7.

2. The synthetic nuclease resistant antisense oligodeoxynucleotide as set forth in claim 1 further including 5'GCCAGAGGAGGAGGAGAAGG 3' SEQ ID No:4,
5'TAGCGTCTACCACCCCTGAC 3' SEQ ID No:5,
5'TCTGTGTTATAGCCCAGCCC 3' SEQ ID No:17, and
5'GGCCTGTAACAGTTTATTT 3' SEQ ID No:18.

3. A nuclease resistant antisense targeted to a splice junction in a splice variant of human AChEmRNA.

4. The nuclease resistant antisense targeted against the splice junction as set forth in claim 3 wherein the E4–E6 junction in the E1–E4–E6 splice variant AChEmRNA is targeted.

5. The nuclease resistant antisense targeted against the splice junction as set forth in claim 3 wherein the E4–E5 junction in the E1–E4–E5 splice variant AChEmRNA is targeted.

6. The nuclease resistant antisense targeted against the splice junction as set forth in claim 3 wherein the E4-I4 junction in the readthrough splice variant AChEmRNA is targeted.

7. A composition comprising as active ingredient at least one synthetic nuclease resistant antisense oligodeoxynucleotide as set forth in claim 1 in a physiologically acceptable carrier or diluent.

8. A composition comprising as active ingredient at least one synthetic nuclease resistant antisense oligodeoxynucleotide as set forth in claim 3 in a physiologically acceptable carrier or diluent.

9. A synthetic nuclease resistant antisense oligodeoxynucleotide for selectively modulating human acetylcholinesterase production in the central nervous system in a mouse selected from the group consisting of 5'ACGCTTTCTTGAGGC 3' SEQ ID No:1,
5'GGCACCCTGGGCAGC 3' SEQ ID No:2
5'CCACGTCCTCCTGCACCGTC 3' SEQ ID No:6,
5'ATGAACTCGATCTCGTAGCC 3' SEQ ID No:7,
5'GCCAGAGGAGGAGGAGAAGG 3' SEQ ID No:4,
5'TAGCGTCTACCACCCCTGAC 3' SEQ ID No:5,
5'TCTGTGTTATAGCCCAGCCC 3' SEQ ID No:17, and
5'GGCCTGTAACAGTTTATTT 3' SEQ ID No:18.

10. A composition comprising as active ingredient at least one synthetic nuclease resistant antisense oligodeoxynucleotide as set forth in claim 9 in a physiologically acceptable carrier or diluent.

11. A method to restore balanced cholinergic signaling in the brain in mice in need of such treatment comprising administering to a mouse in need of such treatment a therapeutically effective amount of at least one of a synthetic nuclease resistant antisense oligodeoxynucleotide according to claim 1.

12. The synthetic nuclease resistant antisense oligodeoxynucleotides as set forth in claim 1 wherein the nuclease resistance is selected from the group consisting of having phosphorothioate bonds linking between the four 3'-terminus nucleotide bases, having a 9 nucleotide loop forming sequence at the 3'-terminus having the nucleotide sequence CGCGAAGCG (SEQ ID No:3), at least one nucleotide is O-methylated, and at least one nucleotide is fluoridated.

13. The synthetic nuclease resistant antisense oligodeoxynucleotides as set forth in claim 3 wherein the nuclease resistance is selected from the group consisting of having phosphorothioate bonds linking between the four 3'-terminus nucleotide bases, having a 9 nucleotide loop forming sequence at the 3'-terminus having the nucleotide sequence CGCGAAGCG (SEQ ID No:3), at least one nucleotide is O-methylated, and at least one nucleotide is fluoridated.

14. A method of determining the efficacy of a synthetic nuclease resistant antisense oligodeoxynucleotide by screening in a transgenic harboring the integrated human AChE gene and in cortico-hippocampal brain slices from a transgenic mouse harboring the integrated human ACHE gene whereby the efficacy of the synthetic nuclease resistant antisense oligodeoxynucleotide to selectively modulate human acetylcholinesterase production can be determined.

* * * * *

UNITED STATES PATENT AND TRADEMARK OFFICE
CERTIFICATE OF CORRECTION

PATENT NO. : 6,121,046
DATED : 09/19/00
INVENTOR(S) : Soreq, et al

It is certified that error appears in the above-identified patent and that said Letters Patent are hereby corrected as shown below:

Column 49, line 43 after "SEQ ID No. 6," insert --and--.
    Column 49, line 45, delete "The" and insert --and--.
        Column 49, line 6, delete "as set forth in claim 1 further including" and insert --for selectively modulating human acetylcholinesterase (AchE) production selected from the group consisting of:--.

Signed and Sealed this

Eighth Day of May, 2001

*Attest:*

NICHOLAS P. GODICI

*Attesting Officer*     *Acting Director of the United States Patent and Trademark Office*